(12) United States Patent
Singh

(10) Patent No.: US 6,682,887 B1
(45) Date of Patent: *Jan. 27, 2004

(54) DETECTION USING DEGRADATION OF A TAGGED SEQUENCE

(75) Inventor: Sharat Singh, San Jose, CA (US)

(73) Assignee: Aclara Biosciences, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/561,579

(22) Filed: Apr. 28, 2000

Related U.S. Application Data

(63) Continuation-in-part of application No. 09/303,029, filed on Apr. 30, 1999, now Pat. No. 6,322,980.

(51) Int. Cl.[7] .......................... C12Q 1/68; C12P 19/34; C07H 21/00; C07H 21/04
(52) U.S. Cl. .................. 435/6; 435/91.2; 536/22.1; 536/23.1; 536/24.3; 536/25.32
(58) Field of Search .................. 535/6, 91.2; 536/22.1, 536/23.1, 24.3, 25.32

(56) References Cited

U.S. PATENT DOCUMENTS

| | | | |
|---|---|---|---|
| 4,274,240 A | 6/1981 | Soum | 52/583 |
| 4,675,300 A | 6/1987 | Zare et al. | 436/172 |
| 5,324,401 A | 6/1994 | Yeung et al. | 204/180.1 |
| 5,560,811 A | 10/1996 | Briggs et al. | 204/451 |
| 5,721,099 A | 2/1998 | Still et al. | 435/6 |
| 5,874,213 A | 2/1999 | Cummins et al. | 435/6 |
| 6,045,676 A | 4/2000 | Mathies et al. | 204/603 |

OTHER PUBLICATIONS

Hacia, J.G., et al., "Detection of heterozygous mutations in BRCA1 using high density oligonucleotide arrays and two–colour fluorescence analysis" *Nature Genetics* 14:441–447 (1996).
Haff, L.A. and Smirnov, I.P., "Multiplex genotyping of PCR products with MassTag–labeled primers" *Nucleic Acids Research* 25(18):3749–3750 (1997).
Lee, L.G., et al., "Allelic discrimination by nick–translation PCR with fluorogenic probes" *Nucleic Acids Research* 21(16):3761–3766 (1993).
Pastinen, T., et al., "Multiplex, fluorescent, solid–phase minisequencing for efficient screening of DNA sequence variation" *Clinical Chemistry* 42(9):1391–1397 (1996).
Ross, P.L., et al., "Discrimination of Single–Nucleotide Polymorphisms in Human DNA Using Peptide Nucleic Acid Probes Detected by MALDI–TOF Mass Spectrometry" *Anal. Chem.* 69:4197–4202 (1997).
White, T.J., "The future of PCR technology: diversification of technologies and applications" *TIBTECH* 14:478–483 (1996).
Woolley, A.T., et al., "Functional Integration of PCR Amplification and Capillary Electrophoresis in a Microfabricated DNA Analysis Device" *Anal. Chem.* 68:4081–4086 (1996).
Haff, *Nucleic Acids Res.* (1997), 25:3749–50.
Holland, *Proc. Acad. Sci. USA* (1991), 88:7276–80.
Houghten, et al., *Int. J. Pep. Prot. Res.* (1980), 16:311–20.
Lee, *Nucleic Acid Research* (1993), 21:16 3761–66.
Marglin, et al., *Ann. Rev. Biochem.* (1970), 39:841–66.
Marino, *Electrophoresis* (1996),17:1499–04.
Matthews, et al., *Anal. Biochem.* (1988), 169:1–25.
Merrifield, *J. Am. Chem. Soc.* (1980), 85:2149–54.
Pastinen, *Clin. Chem.* (1996), 42:1391–97.
Ross, *Anal. Chem.* (1997), 69:4197–4202.
Wetmur, *Critical Rev. in Biochem. And Molecular Biol.* (1991), 26:227–59.
White, *Trends Biotechnology* (1996), 14(12):478–83.
Woolley, et al., *Anal. Chem.* (1996), 68:4081–6.

*Primary Examiner*—Ethan Whisenant
*Assistant Examiner*—Joyce Tung
(74) *Attorney, Agent, or Firm*—Perkins Coie, LLC; Jacqueline Mahoney

(57) ABSTRACT

Methods and compositions are provided for detecting DNA sequences, particularly single nucleotide polymorphisms, using a pair of nucleotide sequences, a primer and a snp detection sequence, where the snp detection sequence binds downstream from the primer to the target DNA in the direction of primer extension. The snp detection sequence is characterized by having a nucleotide complementary to the snp and adjacent nucleotides complementary to adjacent nucleotides in the target and an electrophoretic tag bonded to the 5'-nucleotide. The pair of sequences is combined with the target DNA under primer extension conditions, where the polymerase has 5'-3' exonuclease activity. When the snp is present, the electrophoretic tag is released and can be detected by electrophoresis as indicative of the presence of the snp in the target DNA. The sequence containing the snp is exemplary of DNA sequences of interest generally.

16 Claims, 12 Drawing Sheets

CCA GCA ACC AAT GAT GCC CGT T-TAMARA-3'
CA GCA ACC ATT GAT GCC CGT T-TAMARA-3'

CCA GCA AGC ACT GAT GCC TGT T-TAMARA-3'
CA GCA AGC ACT GAT GCC TGT T-TAMARA-3'

Fig. 1A

|  | Absorbance Maxima | Emission Maxima |
|---|---|---|
| Fluorescein | 494 nm | 525 nm |
| Tetrtachloro Fluorescein | 521 nm | 536 nm |
| TAMRA | 565 nm | 580 nm |

Fig. 1B

DETECTION USING DEGRADATION OF A TAGGED SEQUENCE

CROSS-REFERENCE TO RELATED APPLICATIONS

This application is a continuation-in-part of application Ser. No. 09/303,029, filed Apr. 30, 1999, now U.S. Pat. No. 6,322,980, which disclosure is incorporated herein by reference.

INTRODUCTION

1. Field of the Invention

The field of this invention is multiplex sequence detection, exemplified by single nucleotide polymorphisms and gene expression, using electrophoretic separation.

2. Background of the Invention

As the human genome is elucidated, there will be numerous opportunities for performing assays to determine the presence of specific sequences, distinguishing between alleles in homozygotes and heterozygotes, determining the presence of mutations, evaluating cellular expression patterns, etc. In many of these cases one will wish to determine in a single reaction, a number of different characteristics of the same sample. Also, there will be an interest in determining the presence of one or more pathogens, their antibiotic resistance genes, and the like.

In many assays, there will be an interest in determining the presence of specific sequences, whether genomic or cDNA. These sequences may be associated with particularly genes, regulatory sequences, repeats, multimeric regions, expression patterns, and the like There is and will continue to be comparisons of the sequences of different individuals. It is believed that there will be about one polymorphism per 1,000 bases, so that one may anticipate that there will be an extensive number of differences between individuals. By single nucleotide polymorphism (snp's) is intended that there will be a prevalent nucleotide at the site, with one or more of the remaining bases being present in substantially smaller percent of the population.

For the most part, the snp's will be in non-coding regions, primarily between genes, but will also be present in exons and introns. In addition, the great proportion of the snp's will not affect the phenotype of the individual, but will clearly affect the genotype. The snp's have a number of properties of interest. Since the snp's will be inherited, individual snp's and/or snp patterns may be related to genetic defects, such as detections, insertions and mutations involving one or more bases in genes. Rather than isolating and sequencing the target gene, it will be sufficient to identify the snp's involved.

In addition, the snp's may be used in forensic medicine to identify individuals. While other genetic markers are available, the large number of snp's and their extensive distribution in the chromosomes, make the snp's an attractive target. Also, by determining a plurality of snp's associated with a specific phenotype, one may use the snp pattern as an indication of the phenotype, rather than requiring a determination of the genes associated with the phenotype.

The need to determine many analytes or nucleic acid sequences (for example multiple pathogens or multiple genes or multiple genetic variants) in blood or other biological fluids has become increasingly apparent in many branches of medicine. The need to study differential expression of multiple genes to determine toxicologically-relevant outcomes or the need to screen transfused blood for viral contaminants with high sensitivity is clearly evident.

Thus most multi-analyte assays or assays which detect multiple nucleic acid sequences involve multiple steps, have poor sensitivity and poor dynamic range (2 to 100-fold differences in concentration of the analytes is determined) and some require sophisticated instrumentation.

Some of the known classical methods for multianalyte assays include the following:

a. The use of two different radioisotope labels to distinguish two different analytes.
b. The use of two or more different fluorescent labels to distinguish two or more analytes.
c. The use of lanthanide chelates where both lifetime and wavelength are used to distinguish two or more analytes.
d. The use of fluorescent and chemiluminescent labels to distinguish two or more analytes.
e. The use of two different enzymes to distinguish two or more analytes.
f. The use of enzyme and acridinium esters to distinguish two or more analytes.
g. Spatial resolution of different analytes for example arrays to identify and quantify multiple analytes.
h. The use of acridinium ester labels where lifetime or dioxetanone formation is used to quantify two different viral targets.

Thus an assay that has higher sensitivity, large dynamic range ($10^3$ to $10^4$-fold differences in target nucleic acids levels), and fewer and more stable reagents would increase the simplicity and reliability of multianalyte assays.

The need to identify and quantify a large number of bases or sequences distributed over potentially centimorgans of DNA offers a major challenge. Any method should be accurate, reasonably economical in limiting the amount of reagents required and providing for a single assay, which allows for differentiation of the different snp's or differentiation and quantitation of multiple genes.

BRIEF DESCRIPTION OF THE RELATED ART

Holland (Proc. Natl. Acad. Sci. USA (1991) 88:7276) discloses that the exonuclease activity of the thermostable enzyme Thermus aquaticus DNA polymerase in PCR amplification to generate specific detectable signal concomitantly with amplification.

The TAQMAN assay is discussed by Lee in *Nucleic Acid Research* (1993) 21:16 3761).

White (Trends Biotechnology (1996) 14(12):478–483) discusses the problems of multiplexing in the TAQMAN assay.

Marino, *Electrophoresis* (1996) 17:1499 describes low-stringency-sequence specific PCR (LSSP-PCR). A PCR amplified sequence is subjected to single primer amplification under conditions of low stringency to produce a range of different length amplicons. Different patterns are obtained when there are differences in sequence. The patterns are unique to an individual and of possible value for identity testing.

Single strand conformational polymorphism (SSCP) yields similar results. In this method the PCR amplified DNA is denatured and sequence dependent conformations of the single strands are detected by their differing rates of migration during gel electrophoresis. As with LSSP-PCR above, different patterns are obtained that signal differences in sequence. However, neither LSSP-PCR nor SSCP gives specific sequence information and both depend on the questionable assumption that any base that is changed in a sequence will give rise to a conformational change that can be detected. Pastinen, *Clin. Chem.* (1996) 42:1391 amplifies the target DNA and immobilizes the amplicons. Multiple primers are then allowed to hybridize to sites 3' and contiguous to an SNP site of interest. Each primer has a different size that serves as a code. The hybridized primers are extended by one base using a fluorescently labeled dideoxynucleoside triphosphate. The size of each of the fluorescent products that is produced, determined by gel electrophoresis, indicates the sequence and, thus, the location of the SNP. The identity of the base at the SNP site is defined by the triphosphate that is used. A similar approach is taken by Haff, *Nucleic Acids Res.* (1997) 25:3749 except that the sizing is carried out by mass spectroscopy and thus avoids the need for a label. However, both methods have the serious limitation that screening for a large number of sites will require large, very pure primers that can have troublesome secondary structures and be very expensive to synthesize.

Hacia, *Nat. Genet.* (1996) 14:441 uses a high density array of oligonucleotides. Labeled DNA samples were allowed to bind to 96,600 20-base oligonucleotides and the binding patterns produced from different individuals were compared. The method is attractive in that SNP's can be directly identified but the cost of the arrays is high.

Fan (Oct. 6–8, 1997 IBC, Annapolis Md.) has reported results of a large scale screening of human sequence-tagged sites. The accuracy of single nucleotide polymorphism screening was determined by conventional ABI resequencing.

Allele specific oligonucleotide hybridization along with mass spectroscopy has been discussed by Ross in *Anal. Chem.* (1997) 69:4197.

Holland, et al., PNAS USA (1991) 88, 7276–7280, describes use of DNA polymerase 5'-3' exonuclease activity for detection of PCR products.

SUMMARY OF THE INVENTION

Multiplexed sequence detection, exemplified by snp's and gene expression analysis, is provided by employing a combination of a primer and labeled detector sequence probe in the presence of primer extension reagents, where the polymerase includes 5'-3' exonuclease activity. The labeled detector sequence probe in the case of snps has at least one nucleotide, which is substituted with an electrophoretic tag. One combines the target nucleic acid, which will usually have been processed, with the primer extension reagents and at least one pair for each nucleic acid sequence of interest under conditions for primer extension. After sufficient time for primer extension to occur with degradation of detector sequences bound to target nucleic acid, the electrophoretic tag labeled nucleotides are separated and detected. By having a different electrophoretic tag for each nucleic acid sequence of interest, having a different electrophoretic mobility, which may require further treatment depending on the total number of snp's or target sequences to be detected, one can readily determine the snp's or measure multiple sequences, which are present in a sample..

Electrophoretic tags are small molecules (Molecular weight of 150 to 10,000), usually other than oligonucleotides, which can be used in any measurement technique that permits identification by mass, e.g. mass spectrometry, and or mass/charge ratio, as in mobility in electrophoresis. Simple variations in mass and/or mobility of the electrophoretic tag leads to generation of a library of electrophoretic tags, that can then be used to detect multiple snp's or multiple target sequences. The electrophoretic tags are easily and rapidly separated in free solution without the need for a polymeric separation media. Quantitation is achieved using internal controls. Enhanced separation of the electrophoretic tags in electrophoresis is achieved by modifying the tags with positively charged moieties.

BRIEF DESCRIPTION OF THE DRAWINGS

FIGS. 1A–1C depict the specific sequences of the snp detection sequences for the two alleles (SEQ ID NOs: 3, 4, 52, and 54), the optical characteristics of the fluorescent dyes, and the cleaved fragments from the snp detection sequences, respectively.

DESCRIPTION OF THE SPECIFIC EMBODIMENTS

Figure 1C:
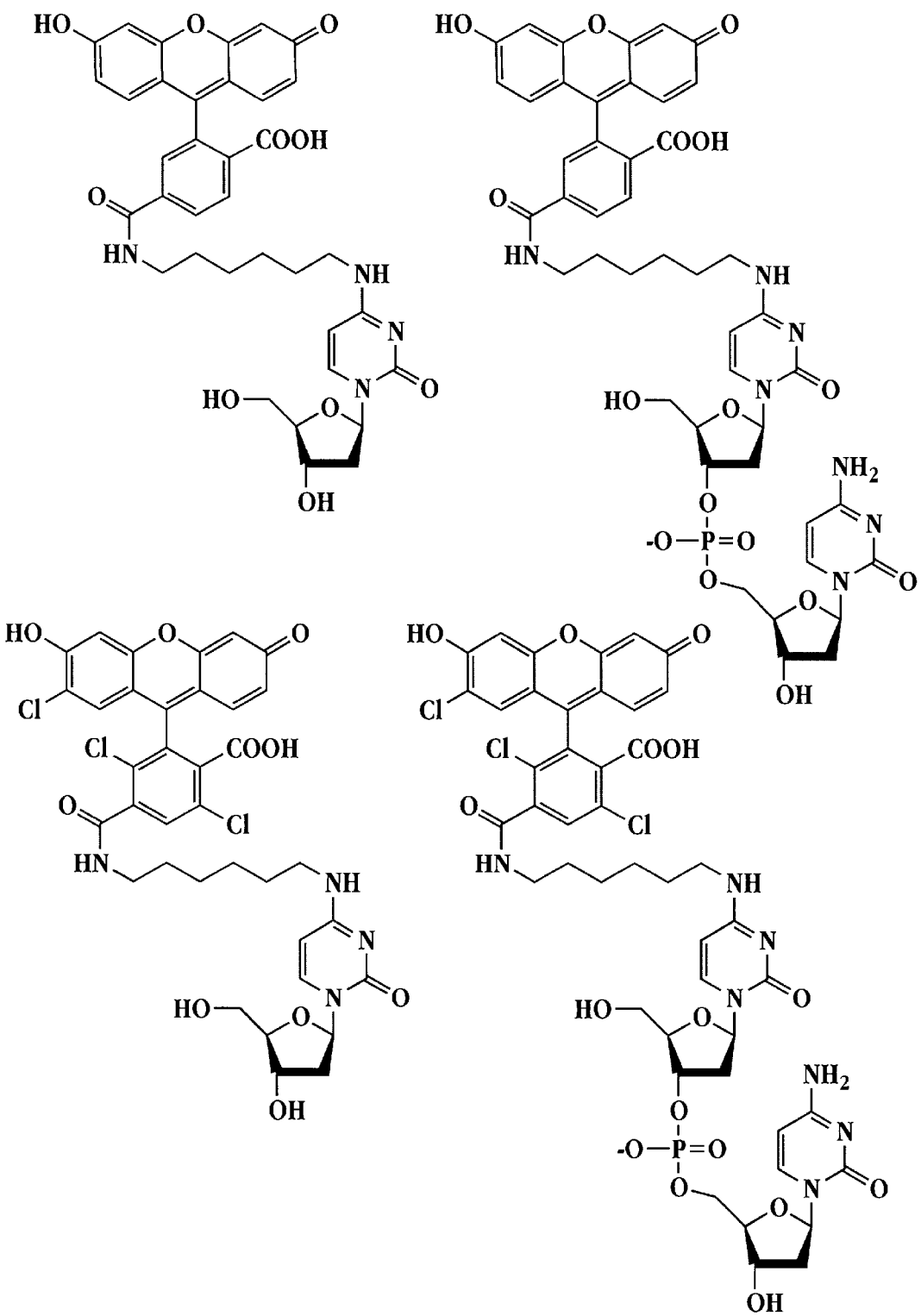

Methods and compositions are provided for improved analysis of complex nucleic acid mixtures, where one is interested in the simultaneous identification of a plurality of entities, such as sequences, snps, alleles, mutations, etc. The methodology involves employing detectable tags that can be differentiated by mass, usually mobility, where the tags are generated by cleavage from a nucleic acid sequence of the probe. Improvements in the detectable tags provide for having a positively multicharged moiety joined to the electrophoretic-tagged probe, employing a blocking linkage between at least the second and third nucleotides to inhibit cleavage at this or subsequent sites, and using control sequences for quantitation. The subject invention may be used for a variety of nucleic acid analyses. However, since snp detection is, for the most part, the most stringent in its requirements, most of the description will be directed toward the multiplexed detection of snps. For other nucleic acid analyses, frequently the protocols will be substantially the same, although in some instances somewhat different protocols will be employed for snps, because of the greater demands snps make on fidelity.

One, usually a plurality, of snp's, is simultaneously determined by combining target DNA with one or a plurality, respectively, of reagent pairs under conditions of primer extension. Each pair of reagents includes a primer which binds to target DNA and a snp detection sequence, normally labeled, which binds to the site of the snp and has an electrophoretic tag, usually at its 5'-end and the base complementary to the snp, usually at other than a terminus of the snp detection sequence. The conditions of primer extension employ a polymerase having 5'-3' exonuclease activity, dNTP's and auxiliary reagents to permit efficient primer extension. The primer extension is performed, whereby detector sequences bound to the target DNA are degraded with release of the electrophoretic tag. By having each snp associated with its own electrophoretic tag, one can determine the snp's, which are present in the target DNA for which pairs of reagents have been provided.

The pairs of reagents are DNA sequences, which are related to a snp site. The primer binds to the target DNA upstream from the snp site in the direction of extension. The labeled detector sequence binds downstream from the primer in the direction of extension and binds to a sequence, which includes the snp. The primer sequence will usually be at least about 12 bases long, more usually at least 18 bases long and usually fewer than 100 bases, and more usually fewer than 60 bases. The primer will be chosen to bind substantially uniquely to a target sequence under the conditions of primer extension, so that the sequence will normally be one that is conserved or the primer is long enough to bind in the presence of a few mismatches, usually fewer than about 10 number % mismatches. By knowing the sequence, which is upstream from the snp of interest, one may select a sequence, which has a high G-C ratio, so as to have a high binding affinity for the target sequence. In addition, the primer should bind reasonably close to the snp, usually not more than about 200 bases away, more usually not more than about 100 bases away, and preferably within about 50 bases. Since the farther away the primer is from the snp, the greater amount of dNTP's, which will be expended, there will usually be no advantage in having a significant distance between the primer and the snp detection sequence. Generally, the primer will be at least about 5 bases away from the snp.

The number of reagent pairs may be varied widely, from a single pair to two or more pairs, usually at least about 5 pairs, more usually at least about 9 pairs and may be 20 pairs or more. By virtue of the use of different E-TAGs, which have different mobilities and are readily resolvable under conventional capillary electrophoretic conditions, the subject pairs may be used to perform multiplexed operations in a single vessel, where a family of snps may be identified. Usually, the total number of different reagent pairs or different target sequences in a single determination will be under 200, more usually under 100 and in many cases will not exceed 50

In one snp determination protocol, the primer terminates prior to the complementary base of the snp. This protocol is referred to as "Invader" technology and is described in U.S. Pat. No. 6,001,567. The protocol involves providing: (a) (i) a cleavage means, which is normally an enzyme, referred to as a cleavase, that recognizes a triplex consisting of the target sequence, a primer which binds to the target sequence and terminates at the snp sequence and a labeled probe that binds immediately adjacent to the primer and is displaced from the target at the snp position, when a snp is present; the cleavase clips the labeled probe at the site of displacement, releasing the label; ii) a source of target nucleic acid, the target nucleic acid having a first region, a second region and a third region, wherein the first region is downstream from the second region and the second region is contiguous to and downstream from the third region; and (iii) first and second oligonucleotides having 3' and 5' portions, wherein the 3' portion of the first oligonucleotide contains a sequence complementary to the third region of the target nucleic acid and the 5' portion of the first oligonucleotide and the 3' portion of the second oligonucleotide each contain sequence fully complementary to the second region of the target nucleic acid, and the 5' portion of the second oligonucleotide contains sequence complementary to the first region of said target nucleic acid; (b) mixing, in any order, the cleavage means, the target nucleic acid, and the first and second oligonucleotides under hybridization conditions that at least the 3' portion of the first oligonucleotide is annealed to the target nucleic acid and at least the 5' portion of the second oligonucleotide is annealed to any target nucleic acid to from a cleavage structure, where the combined melting temperature of the complementary regions within the 5' and 3' portions of the first oligonucleotide when annealed to the target nucleic acid is greater than the melting temperature of the 3' portion of the first oligonucleotide and cleavage of the cleavage structure occurs to generate labeled products; and (c) detecting the labeled cleavage products.

Thus, in an Invader assay attachment of an electrophoretic tag to the 5' end of the detector sequence results in the formation of electrophoretic tag labeled nucleotide when target sequence is present. The electrophoretic tag labeled nucleotide is separated and detected. By having a different electrophoretic tag for each nucleic acid sequence of interest, having a different electrophoretic mobility, which may require further treatment depending on the total number of snp's or target sequences to be detected, one can readily determine the snp's or measure multiple sequences, which are present in a sample.

In another snp detection protocol, an alternative method of cleavage is used and various detectable tags may be employed, the most common using a fluorescent label. The difference in protocol between a fluorescent label and another type of label, such as an electrochemical label, is the method of detection. Otherwise, the protocols will be substantially the same. The tagged snp detection sequence will be chosen to bind to the target sequence comprising the snp. The length of the snp detector sequence is in part related to the length and binding affinity of the primer. The two sequences act together to ensure that the pair of reagents bind to the proper target sequence. The greater the fidelity of binding of one member of the pair, the less fidelity that is required for the other member of the pair. Since the observed signal will be dependent upon both members of the pair being present, each member serves as a check on the other member for production of the signal. However, since except for the cost, it is relatively easy to make reasonably long oligonucleotides, usually both members of the pair will provide for unique binding to their respective target sequences. Therefore, the length of the snp detector sequence will come within the parameters indicated for the primer, but the total number of bases for the two pair members will usually be at least 36, more usually at least about 40.

Each snp detection sequence will have at least one nucleotide modified with an electrophoretic tag, which is labeled, which is fluorescent or can be subsequently made fluorescent, or can be detected electrochemically or by other convenient detection methodologies. Usually, the modified nucleotide will be at the 5'-end of the sequence, but the modified nucleotide may be anywhere in the sequence, particularly where there is a single nuclease susceptible linkage in the detection sequence. Since the determination is based on the at least partial degradation of the snp detector sequence, having the modified nucleotide at the end ensures that if degradation occurs, the electrophoretic tag will be released. Since nucleases may clip at other than the terminal phosphate link, it is desirable to prevent cleavage at other than the terminal phosphate link. In this way one avoids the confusion of having the same electrophoretic tag joined to different numbers of nucleotides after cleavage. Cleavage at the terminal phosphate can be relatively assured by using a linker at the penultimate nucleoside, which is not cleaved by the nuclease, more particularly having only the ultimate linkage susceptible to hydrolysis by a nuclease. For example, one may use a thiophosphate, phosphinate, phosphoramidate, or a linker other than a phosphorous acid derivative, such as an amide, boronate, or the like. The particular hydrolase resistive linker will be primarily one of synthetic convenience, so long as degradation of the binding affinity is not sacrificed. If desired all of the linkers other than the ultimate linker may be resistant to nuclease hydrolysis. The snp detection sequence may be further modified to improve separation and detection of the electrophoretic tags. By virtue of the difference in mobility of the electrophoretic tags, the snp detection sequences will also have different mobilities. Furthermore, these molecules will be present in much larger amounts than the released electrophoretic tags, so that they may obscure detection of the released electrophoretic tags. Also, it is desirable to have negatively charged snp detection sequence molecules, since they provide for higher enzymatic activity and decrease capillary wall interaction. Therefore, by providing that the intact snp detection sequence molecule can be modified with a positively charged moiety, but not the released electrophoretic tag, one can change the electrostatic nature of the snp detection sequence molecules during the separation. By providing for a ligand on the snp detection sequence molecule to which a positively charged molecule can bind, one need only add the positively charged molecule to change the electrostatic nature of the snp detection sequence molecule. Conveniently, one will usually have a ligand of under about 1 kDal. This may be exemplified by the use of biotin as the ligand and avidin, which is highly positively charged, as the receptor/positively charged molecule. Instead of biotin/avidin, one may have other pairs, where the receptor, e.g. antibody, is naturally positively charged or is made so by conjugation with one or more positively charged entities, such as arginine, lysine or histidine, ammonium, etc. The presence of the positively charged moiety has many advantages in substantially removing the snp detection sequence molecules from the electropherogram. In carrying out the process, the positively charged moiety is added at or after the completion of the digestion.

Another way of removing nonspecific degradation products of detection sequence is to attach a ligand, exemplified by biotin, to the penultimate nucleoside. After the 5' nuclease assay, a receptor for the ligand, for biotin exemplified by strept/avidin (hereafter "avidin") is added to the assay mixture. Other receptors include natural or synthetic receptors, such as immunoglobulins, lectins, enzymes, etc. Desirably, the receptor is positively charged, naturally as in the case of avidin, or is made so, by the addition of a positively charged moiety or moieties, such as ammonium groups, basic amino acids, etc. Avidin binds to the biotin attached to the detection probe and its degradation products. Avidin is positively charged, while the cleaved electrophoretic tag is negatively charged. Thus the separation of the cleaved electrophoretic tag from, not only uncleaved probe, but also its degradation products, is easily achieved by using conventional separation methods. Alternatively, the receptor may be bound to a solid support or high molecular weight macromolecule, such as a vessel wall, particles, e.g. magnetic particles, cellulose, agarose, etc., and separated by physical separation or centrifugation, dialysis, etc. This method further enhances the specificity of the assay and allows for a higher degree of multiplexing.

While the ligand may be present at a position other than the penultimate position and one may make the ultimate linkage nuclease resistant, so that cleavage is directed to the penultimate linkage, this will not be as efficient as having cleavage at the ultimate linkage. The efficiency would be even worse where the ligand is at a more distant nucleotide from the E-TAG. Therefore, while such protocols are feasible, and may be used, they will not be preferred.

Where the electrophoretic tags ("E-TAGs") are used for mass detection, as with mass spectrometry, the E-TAGs need not be charged but merely differ in mass, since a charge will be imparted to the E-TAG by the mass spectrometer. The use of the subject method of freeing the E-TAGs of an extended number of nucleotides as a result of cleavage at other than the ultimate linkage finds advantage in any separation technique, where the additional peaks from the series of cleavage products will interfere with analyzing the data, as in mass spectrometry.

The above three methods are generally applicable not only to generating a single electrophoretic tag per sequence detected but also to generation of a single oligonucleotide fragment for fragment separation and identification by electrophoresis or by mass spectra as it is essential to get one fragment per sequence detected. For purpose of explanation, these methods are illustrated below.

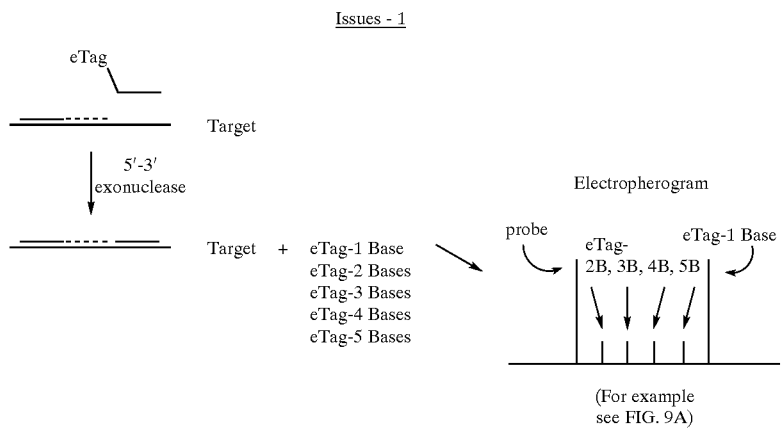

2. Depurination results in degradation of signal probes.
3. Signal probe is also degraded by the enzyme (5'-3' nuclease activity).

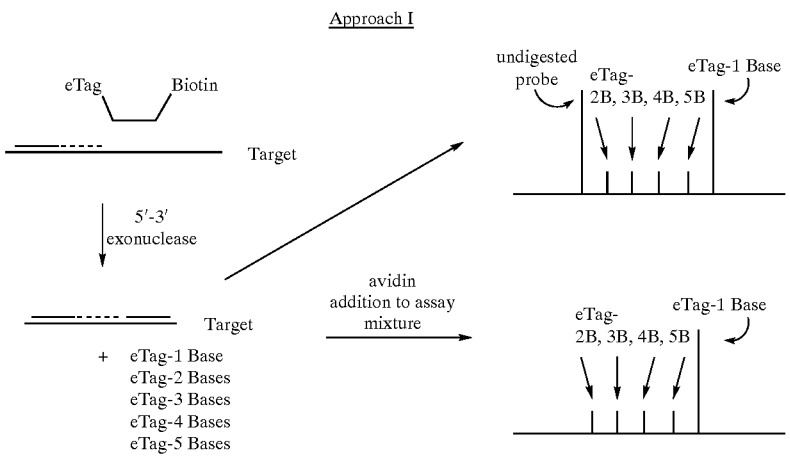

5'-3'-Nucclease Activity.

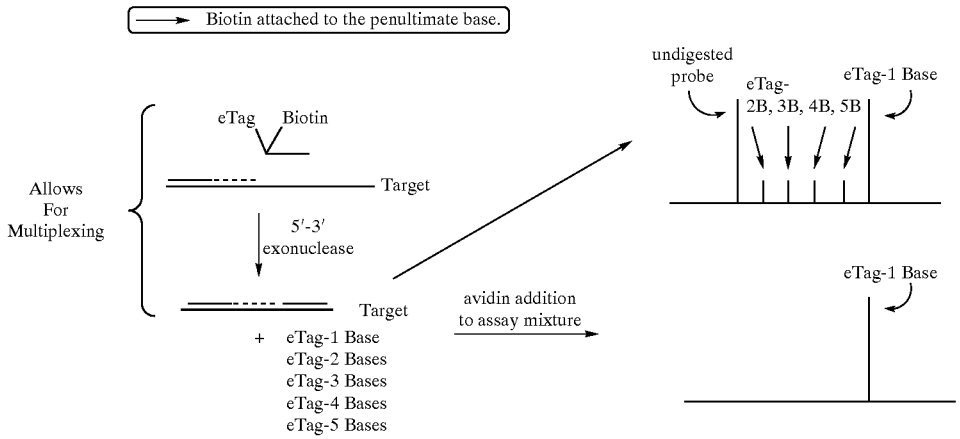

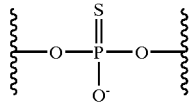

The complementary base to the snp may be anywhere in the detector sequence, desirably at other than the terminal nucleoside to enhance the fidelity of binding. The snp detector sequence will be designed to include adjacent nucleotides, which provide the desired affinity for the hybridization conditions. The snp detection sequence may be synthesized by any convenient means, such as described in Matthews, et al., Anal Biochem. (1988) 169:1–25; Keller, et al., "DNA Probes," 2nd edition (1993) Stockton Press, New York, N.Y.; and Wetmur, Critical Reviews in Biochemistry and Molecular Biology (1991) 26:227–259.

The electrophoretic tag will be one, which is labeled with a directly detectable label or can be made so by functionalization. The electrophoretic tags will be differentiated by their electrophoretic mobility, usually their mass/charge ratio, to provide different mobilities for each electrophoretic tag. Although in some instances the electrophoretic tags may have identical mass/charge ratios, such as oligonucleotides but differ in size or shape and therefore exhibit different electrophoretic mobilities under appropriate conditions. Therefore, the tags will be amenable to electrophoretic separation and detection, although other methods of differentiating the tags may also find use. The electrophoretic tag may be joined to any convenient site on the nucleotide, without interfering with the synthesis of the snp detector sequence and without interfering with the hydrolysis of the phosphate linkage to release the electrophoretic tag. Thus, the tag may be bound to a site on the base, either an annular carbon atom or a hydroxyl or amino substituent. The electrophoretic tag may be linked by a stable bond or one, which may be cleavable, thermally, photolytically or chemically.

There is an interest in cleaving the electrophoretic tag from the nucleotide where the snp detector sequence results in significant cleavage at other than the 5'-phosphate link, resulting in di- and higher oligonucleotides and this family of products interferes with the separation and detection of the electrophoretic tags. However, rather than requiring an additional step in the identification of the tags by releasing them from the base to which they are attached, one can modify the snp detection sequence to minimize obtaining cleavage at other than the ultimate linker.

If present, the nature of the releasable link may be varied widely. Numerous linkages are available, which are thermally, photolytically or chemically labile. See, for example, U.S. Pat. No. 5,721,099. Where detachment of the product is desired, there are numerous functionalities and reactants, which may be used. Conveniently, ethers may be used, where substituted benzyl ether or derivatives thereof, e.g. benzhydryl ether, indanyl ether, etc. may be cleaved by acidic or mild reductive conditions. Alternatively, one may employ beta-elimination, where a mild base may serve to release the product. Acetals, including the thio analogs thereof, may be employed, where mild acid, particularly in the presence of a capturing carbonyl compound, may serve. By combining formaldehyde, HCl and an alcohol moiety, an α-chloroether is formed. This may then be coupled with an hydroxy functionality to form the acetal. Various photolabile linkages may be employed, such as o-nitrobenzyl, 7-nitroindanyl, 2-nitrobenzhydryl ethers or esters, etc.

For a list of cleavable linkages, see, for example, Greene and Wuts, Protective Groups in Organic Synthesis, $2^{nd}$ ed. Wiley, 1991. The versatility of the various systems that have been developed allows for broad variation in the conditions for attachment of the electrophoretic tag entities.

Various functionalities for cleavage are illustrated by: silyl groups being cleaved with fluoride, oxidation, acid, bromine or chlorine; o-nitrobenzyl with light; catechols with cerium salts; olefins with ozone, permanganate or osmium tetroxide; furans with oxygen or bromine in methanol; tertiary alcohols with acid; ketals and acetals with acid; α- and β-substituted ethers and esters with base, where the substituent is an electron withdrawing group, e.g., sulfone, sulfoxide, ketone, etc., and the like.

The electrophoretic tags will have a linker, which provides the linkage between the base and the detectable label molecule, usually a fluorescer, or a functionality which may be used for linking to a detectable label molecule. By having different functionalities, which may be individually bonded to a detectable label molecule, one enhances the opportunity for diversity of the electrophoretic tags. Using different fluorescers for joining to the different functionalities, the different fluorescers can provide differences in light emission and mass/charge ratios for the electrophoretic tags.

The linkers may be oligomers, where the monomers may differ as to mass and charge. For convenience and economy, monomers will generally be commercially available, but if desired, they may be originally synthesized. Monomers which are commercially available and readily lend themselves to oligomerization include amino acids, both natural and synthetic, monosaccharides, both natural and synthetic, while other monomers include hydroxyacids, where the acids may be organic or inorganic, e.g. carboxylic, phosphoric, boric, sulfonic, etc., and amino acids, where the acid is inorganic, and the like. In some instances, nucleotides, natural or synthetic, may find use. The monomers may be neutral, negatively charged or positively charged. Normally, the charges of the monomers in the linkers will be the same, so that in referring to the mass/charge ratio, it will be related to the same charge. Where the label has a different charge from the linker, this will be treated as if the number of charges is reduced by the number of charges on the linker. For natural amino acids, the positive charges may be obtained from lysine, arginine and histidine, while the negative charges may be obtained from aspartic and glutamic acid. For nucleotides, the charges will be obtained from the phosphate and any substituents that may be present or introduced onto the base. For sugars, sialic acid and uronic acids of the various sugars, or substituted sugars may be employed.

For the most part, the linker may be a bond, where the label is directly bonded to the nucleoside, or a link of from 1 to 500 or more, usually 1 to 300 atoms, more usually 2 to 100 atoms in the chain. The total number of atoms in the chain will depend to a substantial degree on the diversity required to recognize all the snp's to be determined. The chain of the linker for the most part will be comprised of carbon, nitrogen, oxygen, phosphorous, boron, and sulfur. Various substituents may be present on the linker, which may be naturally present as part of the naturally occurring monomer or introduced by synthesis. Functionalities which may be present in the chain include amides, phosphate esters, ethers, esters, thioethers, disulfides, borate esters, sulfate esters, etc. The side chains include amines, ammonium salts, hydroxyl groups, including phenolic groups, carboxyl groups, esters, amides, phosphates, heterocycles, particularly nitrogen heterocycles, such as the nucleoside bases and the amino acid side chains, such as imidazole and quinoline, thioethers, thiols, or other groups of interest to change the mobility of the electrophoretic tag. The linker may be a homooligomer or a heterooligomer, having different monomers of the same or different chemical characteristics, e.g., nucleotides and amino acids.

The linker may be joined in any convenient manner to the base of the nucleoside. Various functionalities which may be used include alkylamine, amidine, thioamide, ether, urea, thiourea, guanidine, azo, thioether and carboxylate, sulfonate, and phosphate esters, amides and thioesters.

Besides the nature of the linker, as already indicated, diversity can be achieved by the chemical and optical characteristics of the label, the use of energy transfer complexes, variation in the chemical nature of the linker, which affects mobility, such as folding, interaction with the solvent and ions in the solvent, and the like. As already suggested, the linker will usually be an oligomer, where the linker may be synthesized on a support or produced by cloning or expression in an appropriate host. Conveniently, polypeptides can be produced where there is only one cysteine or serine/threonine/tyrosine, aspartic/glutamic acid, or lysine/arginine/histidine, other than an end group, so that there is a unique functionality, which may be differentially functionalized. By using protective groups, one can distinguish a side chain functionality from a terminal amino acid functionality. Also, by appropriate design, one may provide for preferential reaction between the same functionalities present at different sites on the linking group. Whether one uses synthesis or cloning for preparation of oligopeptides, will to a substantial degree depend on the length of the linker.

The electrophoretic tag, which is detected, will comprise the linker, generally a label, and optionally the nucleotide of the snp detection sequence. Generally, the electrophoretic tag will have a charge/mass ratio in the range of about −0.0001 to 1, usually in the range of about −0.001 to about 0.5. Mobility is $q/M^{2/3}$, where q is the charge on the molecule and M is the mass of the molecule. Desirably, the difference in mobility under the conditions of the determination between the closest electrophoretic labels will be at least about 0.05, more usually at least about 0.1.

If desired, the snp detection sequence may have a combination of a quencher and a fluorescer. In this instance the fluorescer would be in proximity to the nucleoside to which the linker is bonded, as well as the quencher, so that in the primer extension mixture, fluorescence from fluorescer bound to the snp detection sequence would be quenched. As the reaction proceeds and fluorescer is released from the snp detection sequence and, therefore, removed from the quencher, it would then be capable of fluorescence. By monitoring the primer extension mixture for fluorescence, one would be able to determine when there would probably be a sufficient amount of individual electrophoretic tags to provide a detectable signal for analysis. In this way, one could save time and reagent by terminating the primer extension reaction at the appropriate time. There are many quenchers that are not fluorescers, so as to minimize fluorescent background from the snp detection sequence. Alternatively, one could take small aliquots and monitor the reaction for observable electrophoretic tags.

The snp detection sequence may be further modified to improve separation and detection of the electrophoretic tags. By virtue of the difference in mobility of the electrophoretic tags, the snp detection sequences will also have different mobilities. Furthermore, these molecules will be present in much larger amounts than the released electrophoretic tags, so that they may obscure detection of the released electrophoretic tags. Also, it is desirable to have negatively charged snp detection sequence molecules, since they provide for higher enzymatic activity and decrease capillary wall interaction. Therefore, by providing that the intact snp detection sequence molecule can be modified with a positively charged moiety, but not the released electrophoretic tag, one can change the electrostatic nature of the snp detection sequence molecules during the separation. By providing for a ligand on the snp detection sequence molecule to which a positively charged molecule can bind, one need only add the positively charged molecule to change the electrostatic nature of the snp detection sequence molecule. Conveniently, one will usually have a ligand of under about 1 kDal. This may be exemplified by the use of biotin as the ligand and avidin, which is highly positively charged, as the receptor/positively charged molecule. Instead of biotin/avidin, one may have other pairs, where the receptor, e.g. antibody, is naturally positively charged or is made so by conjugation with one or more positively charged entities, such as arginine, lysine or histidine, ammonium, etc. The presence of the positively charged moiety has many advantages in substantially removing the snp detection sequence molecules from the electropherogram. In carrying out the process, the positively charged moiety is added at or after the completion of the digestion.

The extension reaction is performed by bringing together the necessary combination of reagents and subjecting the mixture to conditions for carrying out the desired primer extension. Such conditions depend on the nature of the extension, e.g., PCR, single primer amplification, LCR, NASBA, 3SR and so forth, where the enzyme which is used for the extension has 5'-3' nuclease activity. The extension reaction may be carried out as to both strands or as to only a single strand. Where pairs of primer and snp detection sequence are used for both strands, conveniently, the electrophoretic tag will be the same, but the bases will be different. In this situation, one may wish to have a cleavable linkage to the base, so that for the same snp, one would obtain the same electrophoretic tag. Alternatively, if the number of snp's to be determined is not too high, one could use different electrophoretic tags for each of the strands. Usually, the reaction will be carried out by using amplifying conditions, so as to provide an amplified signal for each snp. Amplification conditions normally employ thermal cycling, where after the primer extension and release of electrophoretic tags associated with snps' which are present, the mixture is heated to denature the double-stranded DNA, cooled, where the primer and snp detection sequence can rehybridize and the extension repeated.

Depending on the protocol, the electrophoretic tags or E-TAG, will be separated from a portion or substantially all of the detection sequence, usually retaining not more than about 3 nucleotides, more usually not more than about 2 nucleotides and preferably from 0 to 1 nucleotide. By having a cleavable linker between the E-TAG and the detection sequence, the E-TAG may be freed of all the nucleotides. By having a nuclease resistant penultimate link, a single nucleotide may be bonded to the E-TAG.

Reagents for conducting the primer extension are substantially the same reaction materials for carrying out an amplification, such as an amplification indicated above. The nature and amounts of these reagents are dependent on the type of amplification conducted. In addition to oligonucleotide primers the reagents also comprise nucleoside triphosphates and a nucleotide polymerase having 5'-3' nuclease activity.

The nucleoside triphosphates employed as reagents in an amplification reaction include deoxyribonucleoside triphosphates such as the four common deoxyribonucleoside triphosphates dATP, dCTP, dGTP and dTTP. The term "nucleoside triphosphates" also includes derivatives and analogs thereof, which are exemplified by those derivatives that are recognized and polymerized in a similar manner to the underivatized nucleoside triphosphates.

The nucleotide polymerase employed is a catalyst, usually an enzyme, for forming an extension of an oligonucleotide primer along a polynucleotide such as a DNA template, where the extension is complementary thereto. The nucleotide polymerase is a template dependent polynucleotide polymerase and utilizes nucleoside triphosphates as building blocks for extending the 3'-end of a polynucleotide to provide a sequence complementary with the polynucleotide template. Usually, the catalysts are enzymes, such as DNA polymerases, for example, prokaryotic DNA polymerase (I, II, or III), T4 DNA polymerase, T7 DNA polymerase, Vent DNA polymerase, Pfu DNA polymerase, Taq DNA polymerase, and the like. Polymerase enzymes may be derived from any source, such as eukaryotic or prokaryotic cells, bacteria such as *E. coli*, plants, animals, virus, thermophilic bacteria, genetically modified enzymes, and so forth.

The conditions for the various amplification procedures are well known to those skilled in the art. In a number of amplification procedures, thermal cycling conditions as discussed above are employed to amplify the polynucleotides. The combination of reagents is subjected to conditions under which the oligonucleotide primer hybridizes to the priming sequence of, and is extended along, the corresponding polynucleotide. The exact temperatures can be varied depending on the salt concentration, pH, solvents used, length of and composition of the target polynucleotide sequence and the oligonucleotide primers.

Thermal cycling conditions are employed for conducting an amplification involving temperature or thermal cycling and primer extension, such as in PCR or single primer amplification, and the like. The pH and the temperature are selected so as to cause, either simultaneously or sequentially, dissociation of any internally hybridized sequences, hybridization or annealing of the oligonucleotide primer and snp detection sequence with the target polynucleotide sequence, extension of the primer, release of the electrophoretic tag from snp detection sequence bound to the target polynucleotide sequence and dissociation of the extended primer. This usually involves cycling the reaction medium among two or more temperatures. In conducting such a method, the medium is cycled between two to three temperatures. The temperatures for thermal cycling generally range from about 50° C. to 100° C., more usually, from about 60° C. to 95° C. Relatively low temperatures of from about 30° C. to about 65° C. can be employed for the extension steps, while denaturation and hybridization can be carried out at a temperature of from about 50° C. to about 105° C. The reaction medium is initially at about 20° C. to about 45° C., preferably, about 25° C. to about 35° C. Relatively low temperatures of from about 50° C. to about 80° C., preferably, 50° C. to about 60° C., are employed for the hybridization or annealing steps, while denaturation is carried out at a temperature of from about 80° C. to about 100° C., preferably, 90° C. to about 95° C., and extension is carried out at a temperature of from about 70° C. to about 80° C., usually about 72° C. to about 74° C. The duration of each cycle may vary and is usually about 1 to 120 seconds, preferably, about 5 to 60 seconds for the denaturation steps, and usually about 1 to 15 seconds, preferably, about 1 to 5 seconds, for the extension steps. It is to be understood that the actual temperature and duration of the cycles employed are dependent on the particular amplification conducted and are well within the knowledge of those skilled in the art.

Generally, an aqueous medium is employed. Other polar cosolvents may also be employed, usually oxygenated organic solvents of from 1–6, more usually from 1–4, carbon atoms, including alcohols, ethers, formamide and the like. Usually, these cosolvents, if used, are present in less than about 70 weight percent, more usually in less than about 30 weight percent.

The pH for the medium is usually in the range of about 4.5 to 9.5, more usually in the range of about 5.5 to 8.5, and preferably in the range of about 6 to 8. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another. The medium may also contain materials required for enzyme activity such as a divalent metal ion (usually magnesium).

The selection of the snp detection sequence will affect the stringency employed during the primer extension, particularly at the stage of hybridization. Since in a substantial number of samples, the DNA will be heterozygous for snps, rather than homozygous, one does not wish to have false positives, where the snp detection sequence may bond to the sequence comprising the prevalent nucleotide, as well as the sequence comprising the snp. Where the DNA sample is homozygous for the prevalent sequence, it is also important that the snp detection sequence does not bind to give a false positive. Therefore, the difference in $T_m$ between the snp containing sequence and the wild-type sequence will usually be at least about 3° C., more usually at least about 5° C., under the conditions of the primer extension.

Various ancillary materials will frequently be employed in the methods in accordance with the present invention. For example, in addition to buffers and salts, the medium may also comprise stabilizers for the medium and the reaction components. Frequently, the medium may also include proteins such as albumins, quaternary ammonium salts, polycations such as spermine, surfactants, particularly non-ionic surfactants, binding enhancers, e.g., polyalkylene glycols, or the like.

The reaction is conducted for a time sufficient to produce the desired number of copies of each of the polynucleotides suspected of being present as discussed below. Generally, the time period for conducting the entire method will be from about 10 to 200 minutes. As mentioned above, it is usually desirable to minimize the time period.

The concentration of the nucleotide polymerase is usually determined empirically. Preferably, a concentration is used that is sufficient such that the amplification is robust. The primary limiting factor generally is the cost of the reagent. Such enzymes include Pfu DNA polymerase (native and recombinant) from Stratagene, La Jolla, Calif., Ultma DNA polymerase from Perkin Elmer, Foster City, Calif., rBst DNA polymerase from Epicentre Technologies, Madison, Wis., VENT DNA polymerase from New England Biolabs, Beverly, Mass., Tli DNA polymerase from Promega Corp., Madison, Wis., and Pwo DNA polymerase from Boehringer Mannheim, Indianapolis; Ind., and the like.

The initial concentration of each of the polynucleotides containing the respective target snps can be as low as about 50 picograms per microliter in a sample. After amplification the concentration of each polynucleotide should be at least about 10 picomolar, generally in the range of about 10 picomolar to about 10 nanomolar, usually from about 10 to $10^{10}$, more usually from about $10^3$ to $10^8$ molecules in a sample preferably at least $10^{-21}$M in the sample and may be $10^{-10}$ to $10^{-9}$M, more usually $10^{-14}$ to $10^{-19}$M. In general, the reagents for the reaction are provided in amounts to achieve extension of the oligonucleotide primers.

The concentration of the oligonucleotide primer(s) will be about 1 to about 20 micromolar and is usually about 1 to about 10 micromolar, preferably, about 1 to about 4 micromolar, for a sample size that is about 10 femtomolar. Preferably, the concentration of the oligonucleotide primer (s) is substantially in excess over, preferably at least about $10^7$ to about $10^{10}$ times greater than, more preferably, at least about $10^9$ times greater than, the concentration of the corresponding target polynucleotides.

The amount of the oligonucleotide probes will be 10 to about 500 nanomolar and is usually about 50 to about 200 nanomolar for a sample size that is about 10 femtomolar (10 femtograms per microliter). Preferably, the concentration of the oligonucleotide probes is substantially in excess over, preferably at least about $10^7$ times greater than, more preferably, at least about $10^8$ times greater than, the concentration of each of the target polynucleotides.

The concentration of the nucleoside triphosphates in the medium can vary widely; preferably, these reagents are present in an excess amount. The nucleoside triphosphates are usually present in about 100 micromolar to about 1 millimolar, preferably, about 20 to about 400 micromolar.

The order of combining of the various reagents to form the combination may vary. Usually, the sample containing the polynucleotides is combined with a pre-prepared combination of nucleoside triphosphates and nucleotide polymerase. The oligonucleotide primers and the snp detection sequences may be included in the prepared combination or may be added subsequently. However, simultaneous addition of all of the above, as well as other step-wise or sequential orders of addition, may be employed provided that all of the reagents described above are combined prior to the start of the reactions. The oligonucleotide pairs may be added to the combination of the reagents at or prior to the initiation of the primer extension reaction and may be replenished from tine-to-time during the primer extension reaction.

For quantitation, one may choose to use controls, which provide a signal in relation to the amount of the target that is present or is introduced. Where one is dealing with a mixture of nucleic acid molecules, as in the case of mRNA in a lysate, one may use the known amounts of one or more different mRNAs in the particular cell types as the standards. Desirably, one would have at least two controls, preferably at least 3 controls, where the variation in number between any two controls is at least about $10^2$, and the total range is at least about $10^3$, usually at least about $10^4$. However, determining the consistent ratio of mRNAs occurring naturally will result in a large margin of error, so that one would usually rely on synthetic targets. Where a control system is added for quantitation, as compared to relying on the presence of a known amount of a plurality of endogenous nucleic acids, the control system will comprise at least two control sequences, usually at least 3 control sequences and generally not more than about 6 control sequences, where the upper limit is primarily one of convenience and economy, since additional control sequences will usually not add significant additional precision. which will usually be at least about 50 nucleotides, more usually at least about 100 nucleotides. The control sequences will have a common primer sequence and different control detection sequences, which are intended to parallel the primer sequence and snp detection sequence in size, spacing and response to the primer extension conditions. In carrying out the primer extension reaction with sample nucleic acid, one would then add different number of molecules of the different control sequences, so that one could graph the result to give a signal/number relationship. This graph could then be used to relate signals observed with target molecules to the number of molecules present.

After completion of the primer extension reaction, either by monitoring the change in fluorescence as described above or taking aliquots and assaying for total free electrophoretic tags, the mixture may now be analyzed. Depending on the instrument, today from one to four different fluorescers activated by the same light source and emitting at different detectable labels may be used. With improvements, five or more different fluorescers will be available, where an additional light source may be required. Electrochemical detection is described in U.S. Pat. No. 6,045,676.

In those instances where a fluorescent label is not present on the electrophoretic tag bound to the snp detection sequence, the mixture may be added to functionalized fluorescent tags to label the electrophoretic tag with a fluorescer. For example, where a thiol group is present, the fluorescer could have an activated ethylene, such as maleic acid to form the thioether. For hydroxyl groups, one could use activated halogen or pseudohalogen for forming an ether, such as an α-haloketone. For carboxyl groups, carbodiimide and appropriate amines or alcohols would form amides and esters, respectively. For an amine, one could use activated carboxylic acids, aldehydes under reducing condtions, activated halogen or pseudohalogen, etc. When synthesizing oligopeptides, protective groups are used. These could be retained while the fluorescent moiety is attached to an available functionality on the oligopeptide.

The presence of each of the cleaved electrophoretic tags is determined by the label. The separation of the mixture of labeled electrophoretic tags is carried out by electroseparation, which involves the separation of components in a liquid by application of an electric field, preferably, by electrokinesis (electrokinetic flow), electrophoretic flow, electroosmotic flow or combination thereof, with the separation of the E-TAG mixture into individual fractions or bands. Electroseparation involves the migration and separation of molecules in an electric field is based on differences in mobility. Various forms of electroseparation include, by way of example and not limitation, free zone electrophoresis, gel electrophoresis, isoelectric focusing and isotachophoresis. Capillary electroseparation involves electroseparation, preferably by electrokinetic flow, including electrophoretic, dielectrophoretic and/or electroosmotic flow, conducted in a tube or channel of about 1–200 micrometer, usually, about 10–100 micrometers cross-sectional dimensions. The capillary may be a long independent capillary tube or a channel in a wafer or film comprised of silicon, quartz, glass or plastic.

In capillary electroseparation, an aliquot of the reaction mixture containing the cleaved labels is subjected to electroseparation by introducing the aliquot into an electroseparation channel that may be part of, or linked to, a capillary device in which the amplification and other reactions are performed. An electric potential is then applied to the electrically conductive medium contained within the channel to effectuate migration of the components within the combination. Generally, the electric potential applied is sufficient to achieve electroseparation of the desired components according to practices well known in the art. One skilled in the art will be capable of determining the suitable electric potentials for a given set of reagents used in the present invention and/or the nature of the cleaved labels, the nature of the reaction medium and so forth. The parameters for the electroseparation including those for the medium and the electric potential are usually optimized to achieve maximum separation of the desired components. This may be achieved empirically and is well within the purview of the skilled artisan.

Capillary devices are known for carrying out amplification reactions such as PCR. See, for example, Analytical Chemistry (1996) 68:4081–4086. Devices are also known that provide functional integration of PCR amplification and capillary electrophoresis in a microfabricated DNA analysis device. One such device is described by Woolley, et al., in Anal. Chem. (1996) 68:4081–4086. The device provides a microfabricated silicon PCR reactor and glass capillary electrophoresis chips. In the device a PCR chamber and a capillary electrophoresis chip are directly linked through a photolithographically fabricated channel filled with a sieving matrix such as hydroxyethylcellulose. Electrophoretic injection directly from the PCR chamber through the cross injection channel is used as an "electrophoretic valve" to couple the PCR and capillary electrophoresis devices on a chip.

The capillary electrophoresis chip contains a sufficient number of main or secondary electrophoretic channels to receive the desired number of aliquots from the PCR reaction medium or the solutions containing the cleaved labels, etc., at the intervals chosen.

For capillary electrophoresis one may employ one or more detection zones to detect the separated cleaved labels. It is, of course, within the purview of the present invention to utilize several detection zones depending on the nature of the amplification process, the number of cycles for which a measurement is to be made and so forth. There may be any number of detection zones associated with a single channel or with multiple channels. Suitable detectors for use in the detection zones include, by way of example, photomultiplier tubes, photodiodes, photodiode arrays, avalanche photodiodes, linear and array charge coupled device (CCD) chips, CCD camera modules, spectrofluorometers, and the like. Excitation sources include, for example, filtered lamps, LED's, laser diodes, gas, liquid and solid state lasers, and so forth. The detection may be laser scanned excitation, CCD camera detection, coaxial fiber optics, confocal back or forward fluorescence detection in single or array configurations, and the like.

Detection may be by any of the known methods associated with the analysis of capillary electrophoresis columns including the methods shown in U.S. Pat. No. 5,560,811 (column 11, lines 19–30), U.S. Pat. Nos. 4,675,300, 4,274,240 and 5,324,401, the relevant disclosures of which are incorporated herein by reference.

Those skilled in the electrophoresis arts will recognize a wide range of electric potentials or field strengths may be used, for example, fields of 10 to 1000 V/cm are used with 200–600 V/cm being more typical. The upper voltage limit for commercial systems is 30 kV, with a capillary length of 40–60 cm, giving a maximum field of about 600 V/cm. For DNA, typically the capillary is coated to reduce electroosmotic flow, and the injection end of the capillary is maintained at a negative potential.

For ease of detection, the entire apparatus may be fabricated from a plastic material that is optically transparent, which generally allows light of wavelengths ranging from 180 to 1500 nm, usually 220 to 800 nm, more usually 450 to 700 nm, to have low transmission losses. Suitable materials include fused silica, plastics, quartz, glass, and so forth.

In mass spectrometry, the E-TAGs may be different from the E-TAGs used in electrophoresis, since the E-TAGs do not require a label, nor a charge. Thus, these E-TAGs may be differentiated solely by mass, which can be a result of atoms of different elements, isotopes of such elements, and numbers of such atoms. In the subject invention, such use of E-TAGs will be coupled with a process for removing the iterative extensions of the nucleic acid sequence, where degradation or cleavage has occurred at a site other than the ultimate linkage.

The electrophoretic tag for use in electrophoresis may be represented by the formula:

wherein R is a label, particularly a fluorescer, L is a bond or a linking group as described previously, and T comprises a nucleoside base, purine or pyrimidine, and is the base, a nucleoside, nucleotide or nucleotide triphosphate, when the base is retained and is otherwise a functionality resulting from the cleavage. L provides a major factor in the differences in mobility between the different electrophoretic tags, in combination with the label and any nucleotides, which remain with the linker. L may or may not include a cleavable linker, depending upon whether the terminal nucleotide(s) are to be retained or completely removed.

The linker L may include charged groups, uncharged polar groups or be non-polar. The groups may be alkylene and substituted alkylenes, oxyalkylene and polyoxyalkylene, particularly alkylene of from 2 to 3 carbon atoms, arylenes and substituted arylenes, polyamides, polyethers, polyalkylene amines, etc. Substituents may include heteroatoms, such as halo, phosphorous, nitrogen, oxygen, sulfur, etc., where the substituent may be halo, nitro, cyano, non-oxo-carbonyl, e.g. ester, acid and amide, oxo-carbonyl, e.g. aldehyde and keto, amidine, urea, urethane, guanidine, carbamyl, amino and substituted amino, particularly alkyl substituted amino, azo, oxy, e.g. hydroxyl and ether, etc., where the substituents will generally be of from about 0 to 10 carbon atoms, while the linking group will generally be of from about 1 to 100 carbon atoms, more usually of from about 1 to 60 carbon atoms and preferably about 1 to 36 carbon atoms. The linking group will be joined to the label and the nucleotide by any convenient functionality, such as carboxy, amino, oxy, phospo, thio, iminoether, etc., where in many cases the label and the nucleotide will have a convenient functionality for linkage.

The number of heteroatoms in L is sufficient to impart the desired charge to the label conjugate, usually from about 1 to about 200, more usually from about 2 to 100, heteroatoms. The heteroatoms in L may be substituted with atoms other than hydrogen.

The charge-imparting moieties of L may be, for example, amino acids, tetraalkylammonium, phosphonium, phosphate diesters, carboxylic acids, thioacids, sulfonic acids, sulfate groups, phosphate monoesters, and the like and combinations of one or more of the above. The number of the above components of L is such as to achieve the desired number of different charge-imparting moieties. The amino acids may be, for example, lysine, aspartic acid, alanine, gamma-aminobutyric acid, glycine, β-alanine, cysteine, glutamic acid, homocysteine, β-alanine and the like. The phosphate diesters include, for example, dimethyl phosphate diester, ethylene glycol linked phosphate diester, and so forth. The thioacids include, by way of example, thioacetic acid, thiopropionic acid, thiobutyric acid and so forth. The carboxylic acids preferably have from 1 to 30 carbon atoms, more preferably, from 2 to 15 carbon atoms and preferably comprise one or more heteroatoms and may be, for example, acetic acid derivatives, formic acid derivatives, succinic acid derivatives, citric acid derivatives, phytic acid derivatives and the like. In one embodiment of the present invention the label conjugates having different charge to mass ratios may comprise fluorescent compounds, each of which are linked to molecules that impart a charge to the fluorescent compound conjugate. As indicated previously, desirably the linking group has an overall negative charge, preferably having in the case of a plurality of groups, groups of the same charge, where the total charge may be reduced by having one or more positively charged moiety.

Combinations of particular interest comprise a fluorescent compound and a different amino acid or combinations thereof in the form of a peptide or combinations of amino acids and thioacids or other carboxylic acids. Such compounds are represented by the formula:

wherein R' is a fluorescer, L' is is an amino acid or a peptide or combinations of amino acids and thioacids or other carboxylic acids and T' is a functionality for linking to a nucleoside base or is a nucleoside, nucleotide or nucleotide triphosphate.

In a preferred embodiment of the present invention, the charge-imparting moiety is conveniently composed primarily of amino acids but also may include thioacids and other carboxylic acids having from one to five carbon atoms. The charge imparting moiety may have from 1 to 30, preferably 1 to 20, more preferably, 1 to 10 amino acids per moiety and may also comprise 1 to 3 thioacids or other carboxylic acids. As mentioned above, any amino acid, both naturally occurring and synthetic may be employed.

In a particular embodiment the label conjugates may be represented by the formula:

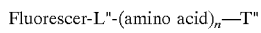

Fluorescer-L"-(amino acid)$_n$—T"

wherein L" is a bond or a linking group of from 1 to 20 atoms other than hydrogen, n is 1 to 20, and T" comprises a nucleoside base, purine or pyrimidine, including a base, a nucleoside, a nucleotide or nucleotide triphosphate. An example of label conjugates in this embodiment, by way of illustration and not limitation, is one in which the fluorescer is fluorescein, L" is a bond in the form of an amide linkage involving the meta-carboxyl of the fluorescein and the terminal amine group of lysine, and T" is a nucleotide triphosphate. These label conjugates may be represented as follows:

Fluorescein-(CO)NH—CH(CH$_2$)$_3$CH(NH$_2$)(amino acid)$_n$COT" wherein X is as set forth in Table 1.

TABLE 1

| No. | X | Charge |
|---|---|---|
| 1 | OH | −2 |
| 2 | NH-lysine | −1 |
| 3 | NH-(lysine)$_2$ | neutral |
| 4 | NH-alanine | −3 |
| 5 | NH-aspartic acid | −4 |
| 6 | NH-(aspartic acid)$_2$ | −5 |
| 7 | NH-(aspartic acid)$_3$ | −6 |
| 8 | NH-(aspartic acid)$_4$ | −7 |
| 9 | NH-(aspartic acid)$_5$ | −8 |
| 10 | NH-(aspartic acid)$_6$ | −9 |
| 11 | NH-(aspartic acid)$_7$ | −10 |
| 12 | NH-alanine-lysine | −2 (unique q/M) |
| 13 | NH-aspartic acid-lysine | −3 (unique q/M) |
| 14 | NH-(aspartic acid)$_2$-lysine | −4 (unique q/M) |
| 15 | NH-(aspartic acid)$_3$-lysine | −5 (unique q/M) |
| 16 | NH-(aspartic acid)$_4$-lysine | −6 (unique q/M) |
| 17 | NH-(aspartic acid)$_5$-lysine | −7 (unique q/M) |
| 18 | NH-(aspartic acid)$_6$-lysine | −8 (unique q/M) |
| 19 | NH-(aspartic acid)$_7$-lysine | −9 (unique q/M) |
| 20 | NH-(aspartic acid)$_8$-lysine | −10 (unique q/M) |
| 21 | NH-(lysine)$_4$ | 1 |
| 22 | NH-(lysine)$_5$ | +2 | wherein q is charge, M is mass and mobility is $q/M^{2/3}$. Examples of such label conjugates are shown in FIG. 1C.

Table 2 shows various characteristics for the label conjugates.

TABLE 2

| No. | Mass(M) | Charge(q) | $M^{2/3}$ | $q/M^{2/3}$ | Mobility |
|---|---|---|---|---|---|
| 1 | 744.82 | 0 | 82.16765 | 0 | 0 |
| 2 | 877.02 | 0 | 91.62336 | 0 | 0 |
| 3 | 828.71 | −1 | 88.22704 | −0.01133 | −0.16546 |
| 4 | 970.71 | −1 | 98.03767 | −0.0102 | −0.1489 |
| 5 | 700.82 | −2 | 78.89891 | −0.02535 | −0.37004 |
| 6 | 842.83 | −2 | 89.22639 | −0.2241 | −0.32721 |
| 7 | 815.92 | −3 | 87.31692 | −0.03436 | −0.50155 |

TABLE 2-continued

| No. | Mass(M) | Charge(q) | $M^{2/3}$ | $q/M^{2/3}$ | Mobility |
|---|---|---|---|---|---|
| 8 | 957.92 | −3 | 97.17461 | −0.03087 | −0.45067 |
| 9 | 931.02 | −4 | 95.34677 | −0.04195 | −0.61242 |
| 10 | 1073.02 | −4 | 104.8106 | −0.03816 | −0.55712 |
| 11 | 1046 | −5 | 103.0436 | −0.04852 | −0.70834 |
| 12 | 1188 | −5 | 112.1702 | −0.04458 | −0.65071 |
| 13 | 1161 | −6 | 110.4642 | −0.05432 | −0.79291 |
| 14 | 1303 | −6 | 119.297 | −0.05029 | −0.7342 |
| 15 | 1276 | −7 | 117.6433 | −0.0595 | −0.86861 |
| 16 | 1418 | −7 | 126.2169 | −0.05546 | −0.80961 |
| 17 | 1391 | −8 | 124.6096 | −0.0642 | −0.9372 |
| 18 | 1533 | −8 | 132.952 | −0.06017 | −0.87839 |
| 19 | 1506 | −9 | 131.3863 | −0.0685 | −0.99997 |
| 20 | 1648 | −9 | 139.6205 | −0.06451 | −0.94167 |
| 21 | 793.52 | 1 | 85.7114 | 0.011667 | 0.170316 |
| 22 | 935.52 | 1 | 95.65376 | 0.010454 | 0.152613 |

The label conjugates may be prepared utilizing conjugating techniques that are well known in the art. The charge-imparting moiety L may be synthesized from smaller molecules that have functional groups that provide for linking of the molecules to one another, usually in a linear chain. Such functional groups include carboxylic acids, amines, and hydroxy- or thiol-groups. In accordance with the present invention the charge-imparting moiety may have one or more side groups pending from the core chain. The side groups have a functionality to provide for linking to a label or to another molecule of the charge-imparting moiety.

Common functionalities resulting from the reaction of the functional groups employed are exemplified by forming a covalent bond between the molecules to be conjugated. Such functionalities are disulfide, amide, thioamide, dithiol, ether, urea, thiourea, guanidine, azo, thioether, carboxylate and esters and amides containing sulfur and phosphorus such as, e.g. sulfonate, phosphate esters, sulfonamides, thioesters, etc., and the like.

The chemistry for performing the types of syntheses to form the charge-imparting moiety as a peptide chain is well known in the art. See, for example, Marglin, et al., *Ann. Rev. Biochem.* (1970) 39:841–866. In general, such syntheses involve blocking, with an appropriate protecting group, those functional groups that are not to be involved in the reaction. The free functional groups are then reacted to form the desired linkages. The peptide can be produced on a resin as in the Merrifield synthesis (Merrifield, *J. Am. Chem. Soc.* (1980) 85:2149–2154 and Houghten et al., *Int. J. Pep. Prot. Res.* (1980) 16:311–320. The peptide is then removed from the resin according to known techniques.

A summary of the many techniques available for the synthesis of peptides may be found in J. M. Stewart, et al., "Solid Phase Peptide Synthesis, W. H. Freeman Co, San Francisco (1969); and J. Meienhofer, "Hormonal Proteins and Peptides", (1973), vol. 2, p 46., Academic Press (New York), for solid phase peptide synthesis and E. Schroder, et al.,"The Peptides, vol. 1, Academic Press (New York), 1965 for solution synthesis.

In general, these methods comprise the sequential addition of one or more amino acids, or suitably protected amino acids, to a growing peptide chain. Normally, a suitable protecting group protects either the amino or carboxyl group of the first amino acid. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide. The protecting groups are removed, as desired, according to known methods depending on the particular protecting group utilized. For example, the protecting group may be removed by reduction with hydrogen and palladium on charcoal, sodium in liquid ammonia, etc.; hydrolysis with trifluoroacetic acid, hydrofluoric acid, and the like.

After the synthesis of the peptide is complete, the peptide is removed from the resin by conventional means such as ammonolysis, acidolysis and the like. The fully deprotected peptide may then be purified by techniques known in the art such as chromatography, for example, adsorption chromatography; ion exchange chromatography, partition chromatography, high performance liquid chromatography, thin layer chromatography, and so forth.

As can be seen, the selected peptide representing a charge-imparting moiety may be synthesized separately and then attached to the label either directly or by means of a linking group. On the other hand, the peptide may be synthesized as a growing chain on the label. In any of the above approaches, the linking of the peptide or amino acid to the label may be carried out using one or more of the techniques described above for the synthesis of peptides or for linking moieties to labels.

The aforementioned label conjugates with different electrophoretic mobility permit a multiplexed amplification and detection of multiple single nucleotide polymorphisms. The label conjugates are linked to oligonucleotides in a manner similar to that for labels in general, by means of linkages that are enzymatically cleavable. It is, of course, within the purview of the present invention to prepare any number of label conjugates for performing multiplexed determinations. Accordingly, for example, with 40 to 50 different label conjugates separated in a single separation channel and 96 different amplification reactions with 96 separation channels on a single plastic chip, one can detect 4000 to 5000 single nucleotide polymorphisms.

As exemplary of the subject invention, four target polynucleotides T1, T2, T3 and T4 are employed. Oligonucleotide primers PR1, PR2, PR3 and PR4 are employed, each respectively capable of hybridizing to a sequence in the respective target polynucleotides. Also employed are four oligonucleotide snp detection sequences, PB1, PB2, PB3 and PB4. Each of the snp detection sequences comprises a fluorescent label F1, F2, F3 and F4, respectively. In this example, there is a mismatch between PB2 and T2, which comprises a single nucleotide polymorphism. The reaction medium comprising the above reagents and nucleoside triphosphates and a template dependent polynucleotide polymerase having 5' to 3' exonuclease activity is treated under amplification conditions. Primers PR1, PR2, PR3 and PR4 hybridize to their respective target polynucleotides and are extended to yield extended primers EPR1, EPR2, EPR3 and EPR4. snp detection sequences PB1, PB3 and PB4, which hybridize with their respective target polynucleotides, are acted upon by the exonuclease to cleave a single nucleotide bearing the respective fluorescent label. PB2, which does not bind to the target polynucleotide, is not cleaved. Cleaved fragments F1, F3 and F4 are injected into a separation channel in a chip for conducting electroseparation. The labels are identified by their specific mobility and fluorescence upon irradiation. The separated labels are related to the presence and amount of the respective target polynucleotide.

Synthesis of electrophoretic tags can be most easily and effectively achieved via assembly on a solid phase support during probe synthesis using standard phosphoramdite chemistries. The concept hinges on the formation of a unique electrophoretic tags during an $S_1$ nuclease digest of the probe. It is important to note that only the 5'-terminal base paired residue of the probe is cleaved. As such, any components bound to the terminal residue which do not form base pairs will be released as well. Therefore, electrophoretic tags can be assembled by the coupling of a penultimate unique base pairing residue followed by a final coupling of a dye residue containing a phosphoramidite handle. The electrophoretic tags is thus composed of two units of variable charge to mass ratios bridged by a phosphate linker (See below).

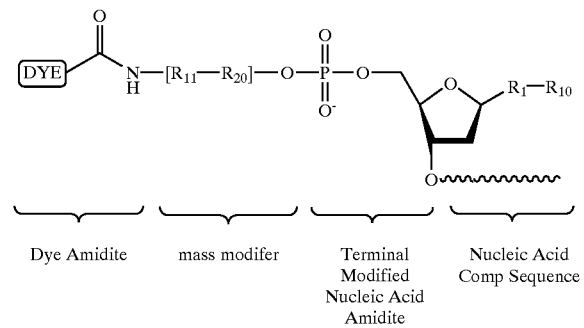

Dye Amidite    mass modifer    Terminal Modified Nucleic Acid Amidite    Nucleic Acid Comp Sequence The design and synthesis of electrophoretic tags on solid phase support using standard phosphoramidite coupling chemistry.

The separation of electrophoretic tags, which differ by 9 mass units (Table 1) has been demonstrated FIG. 7. The penultimate coupling during probe synthesis is initially carried out using commercially available modified (and unmodified) phosphoramidites (Table 2). This residue is able to form hydrogen bonds to its partner in the target strand and is considered a mass modifier but could potentially be a charge modifier as well. The phosphate bridge formed during this coupling is the linkage severed during the 5'-nuclease assay. The final coupling is done using a phosphoramidite analogue of a dye. Fluorescein is conveniently employed, but other dyes can be used as well.

The initial synthetic approach is outlined in Scheme 1. Starting with commercially available 6-carboxy fluorescein, the phenolic hydroxyl groups are protected using an anhydride. Isobutyric anhydride in pyridine was employed but other variants are equally suitable. It is important to note the significance of choosing an ester functionality as the protecting group. This species remains intact though the phosphoramidite monomer synthesis as well as during oligonucleotide construction. These groups are not removed until the synthesized oligo is deprotected using ammonia. After protection the crude material is then activated in situ via formation of an N-hydroxy succinimide ester (NHS-ester) using DCC as a coupling agent. The DCU byproduct is filtered away and an amino alcohol is added. Many amino alcohols are

| E-Tag | Elution Time on CE (sec) | Mass |
|---|---|---|
| | 385 | 778 |
| | 428 | 925 |
| | 438 | 901 |

| E-Tag | Elution Time on CE (sec) | Mass |
|---|---|---|
| 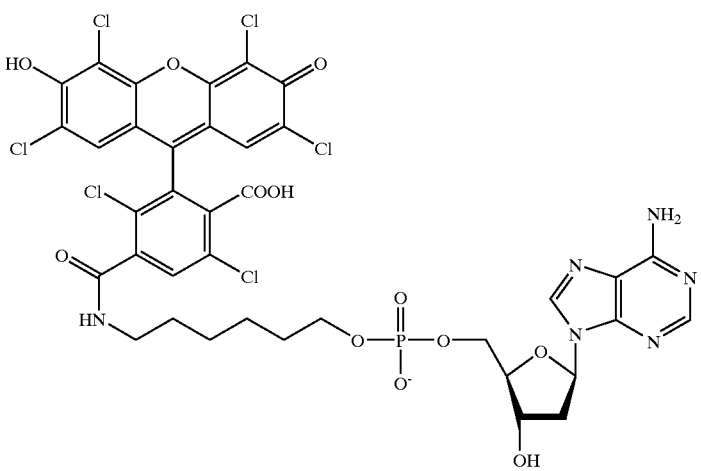 | 462 | 994 |
| 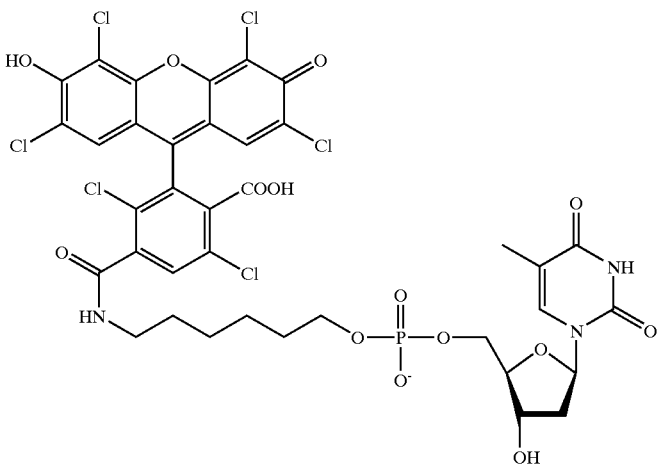 | 480 | 985 |
| 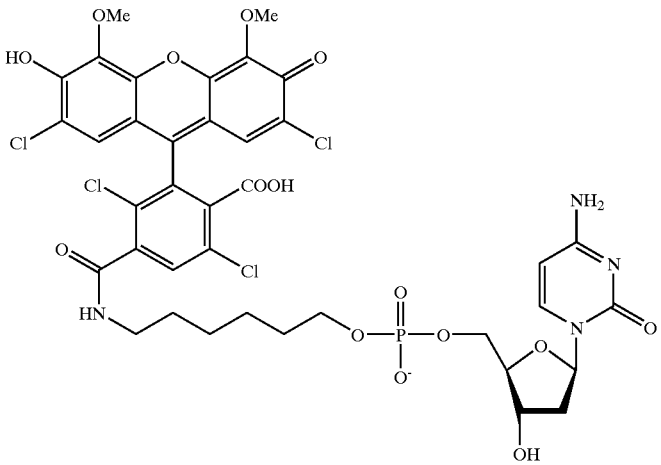 | 555 | 961 |

TABLE 1
E-Tags that have been separated on a LabCard (detection: 4.7 cm; 200 V/cm).
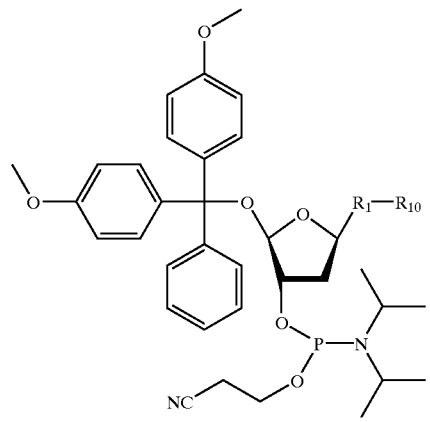
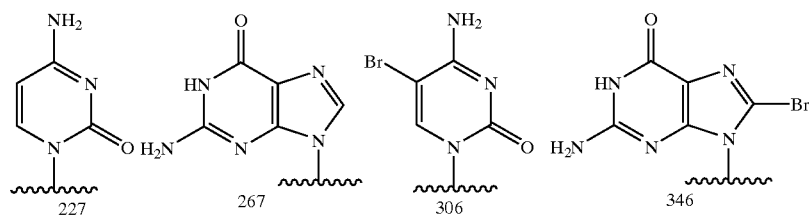
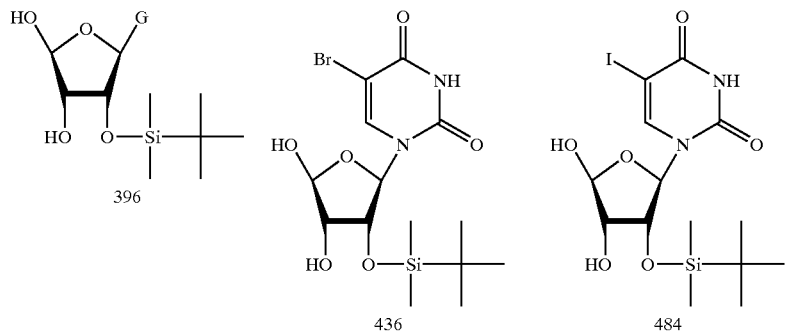
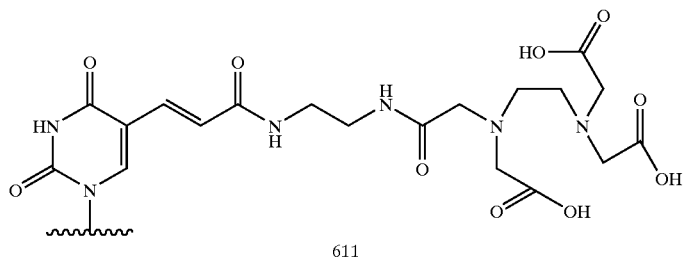

Table 2. Potential mass and charged modified nucleic acid phosphoramidites to be employed as the penultimate coupling during probe synthesis on a standard DNA synthesizer.

Commercially available some of which are derived from reduction of amino acids. Only the amine is reactive enough to displace N-hydroxy succinimide. Upon standard Scheme 1

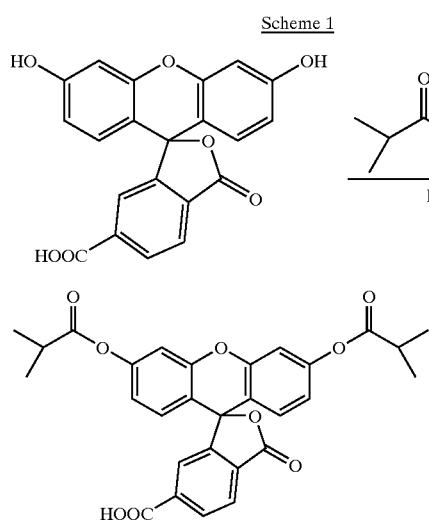

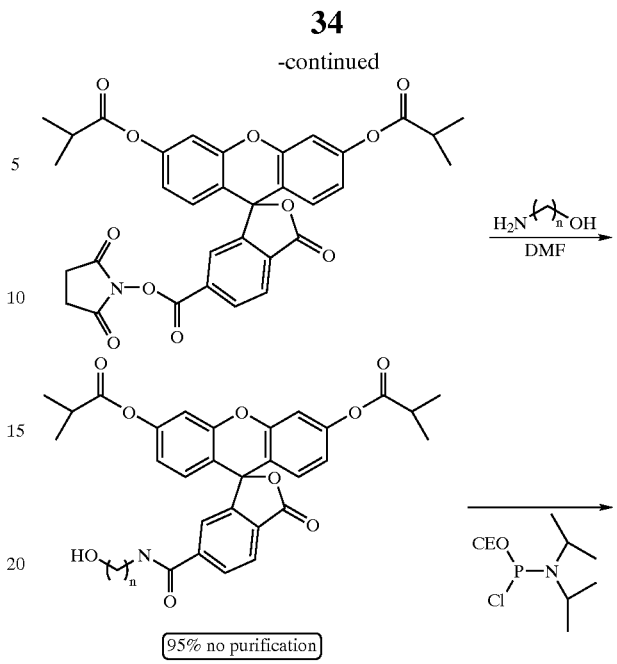

extractive workup, a 95% yield of product is obtained. This material is phosphitylated to generate the phosphoramidite monomer (Scheme 1). For the synthesis of additional E-Tags, a symmetrical bisamino alcohol linker is used as the amino alcohol (Scheme 2). As such the second amine is then coupled with a multitude of carboxylic acid derivatives (Table 3) prior to the phosphitylation reaction. Using this methodology hundreds if not thousands of E-TAGs with varying charge to mass ratios can easily be assembled during probe synthesis on a DNA synthesizer using standard chemistries.

Scheme 2

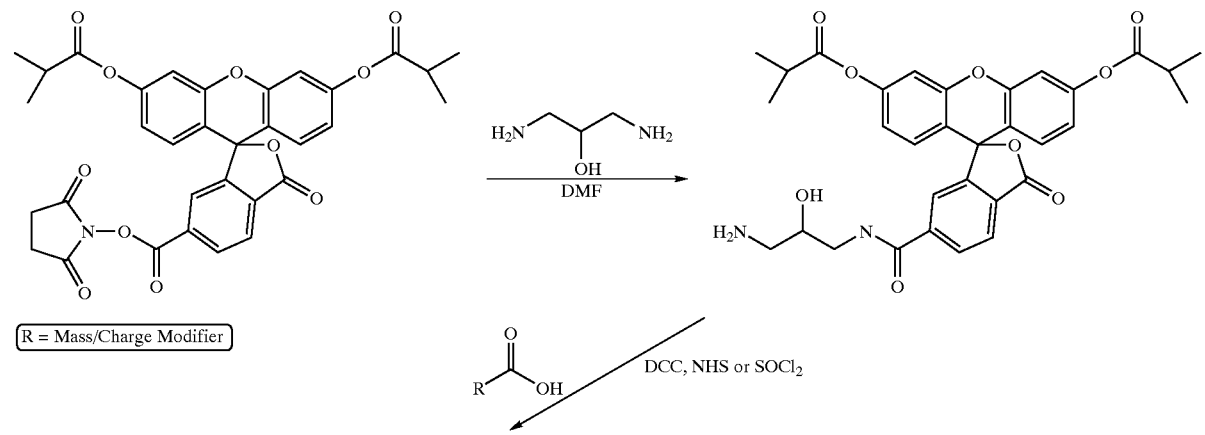

-continued

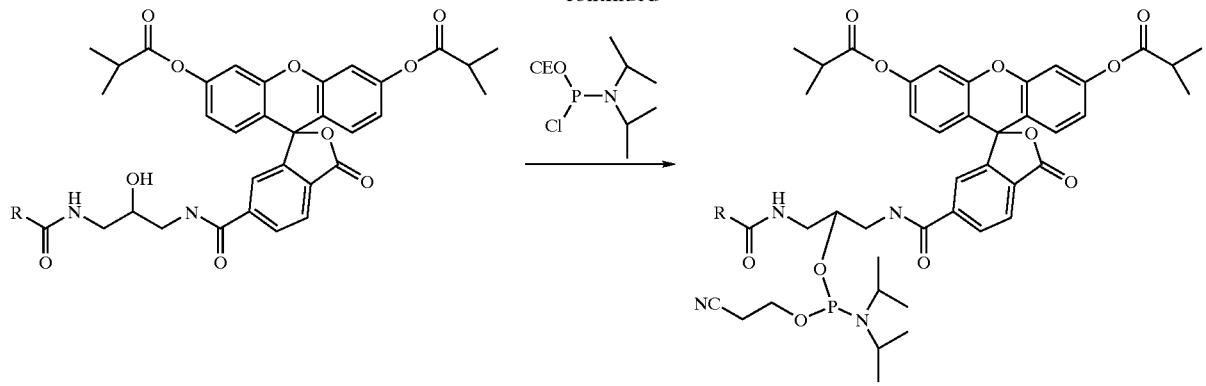

Additional electrophoretic tags are accessed via an alternative strategy which uses 5-aminofluorescein as stating material (Scheme 3). Addition of 5-aminofluorescein to a great excess of a diacid chloride in a large volume of solvent allows for the predominant formation of the monoacylated product over dimmer formation. The phenolic groups are not reactive under these conditions. Aqueous workup converts the terminal acid chloride to a carboxylic acid. This product is analogous to 6-carboxy fluorescein and using the same series of steps is converted to its protected phosphoramidite monomer (Scheme 3). There are many commercially available di(acid chorides) and diacids, which can be converted to diacid chlorides using $SOCl_2$ or acetyl chloride. This methodology is highly attractive in that a second mass modifier is used. As such, if one has access to 10 commercial modified phosphoramidites and 10 diacid chlorides and 10 amino alcohols there is a potential for 1000 different E-Tags. There are many commercial diacid chlorides and amino alcohols (Table 4). These synthetic approaches are ideally suited for combinatorial chemistry.

Scheme 3

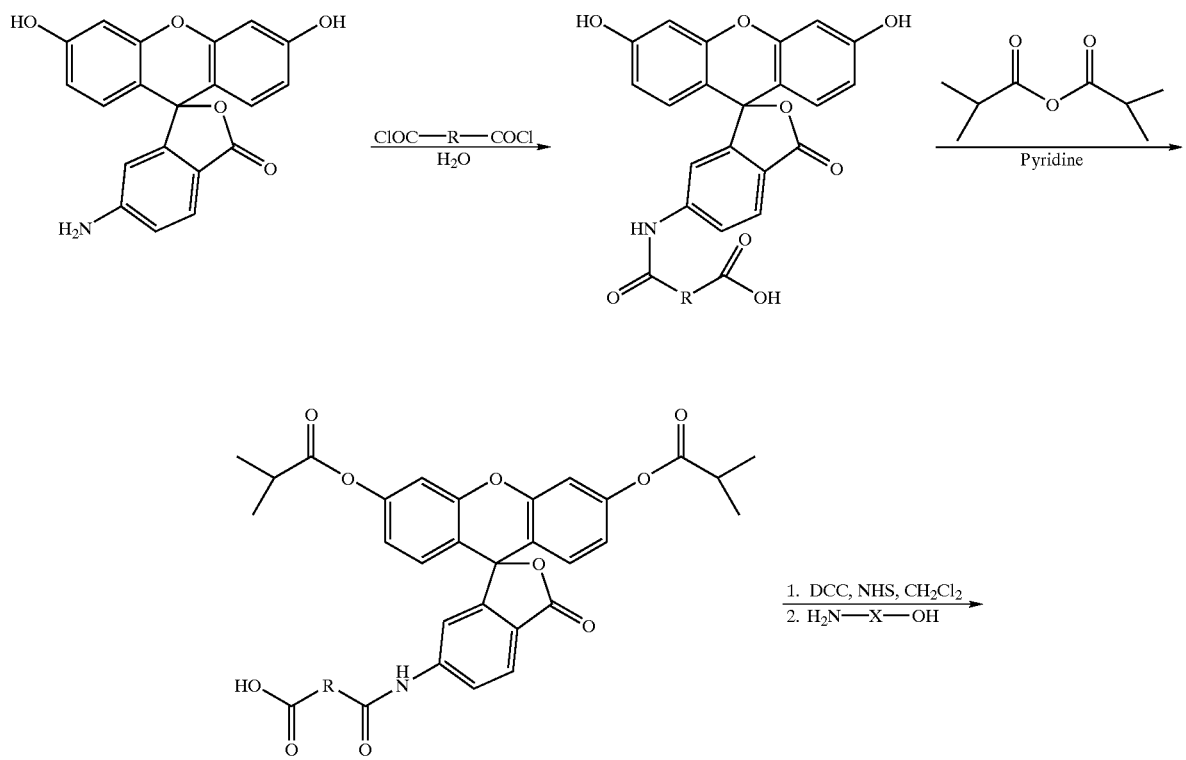

-continued
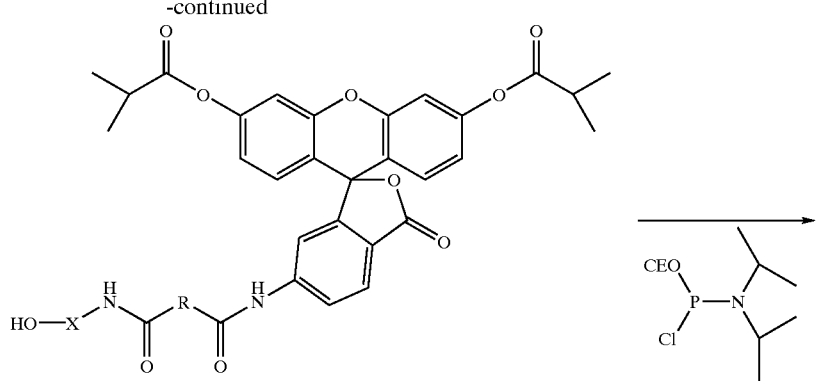
R = commercial diacidchloride
X = commercial amino alcohol
TABLE 3
Benzoic acid derivatives as mass and charge modifiers. (Mass is written below each modifier)
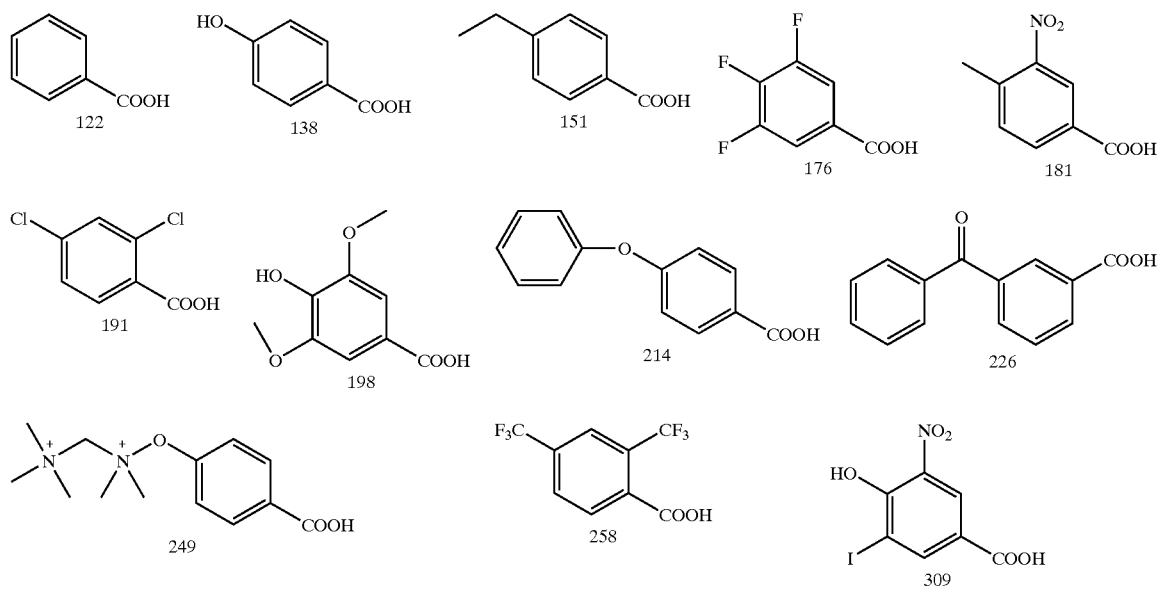
TABLE 4
Mass and charge modifiers that can be used for conversion of amino dyes into E-Tag phosphoramidite monomers.
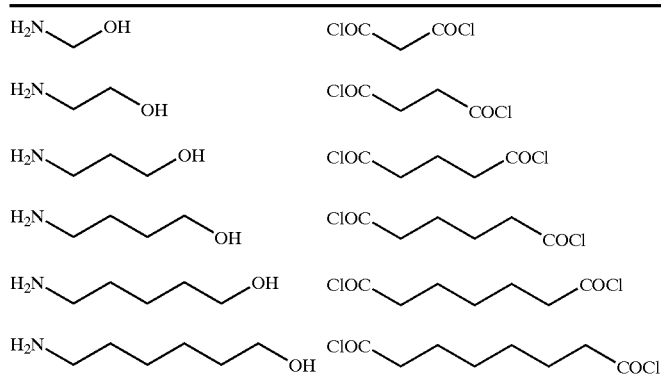

TABLE 4-continued

Mass and charge modifiers that can be used for conversion of amino dyes into E-Tag phosphoramidite monomers.

A variety of maleimide derivatized E-Tags have also been synthesized. These compounds were subsequently bioconjugated to 5'-thiol adorned DNA sequences and subjected to the 5'-nuclease assay. The species formed upon cleavage are depicted in

TABLE 5

TABLE 5-continued
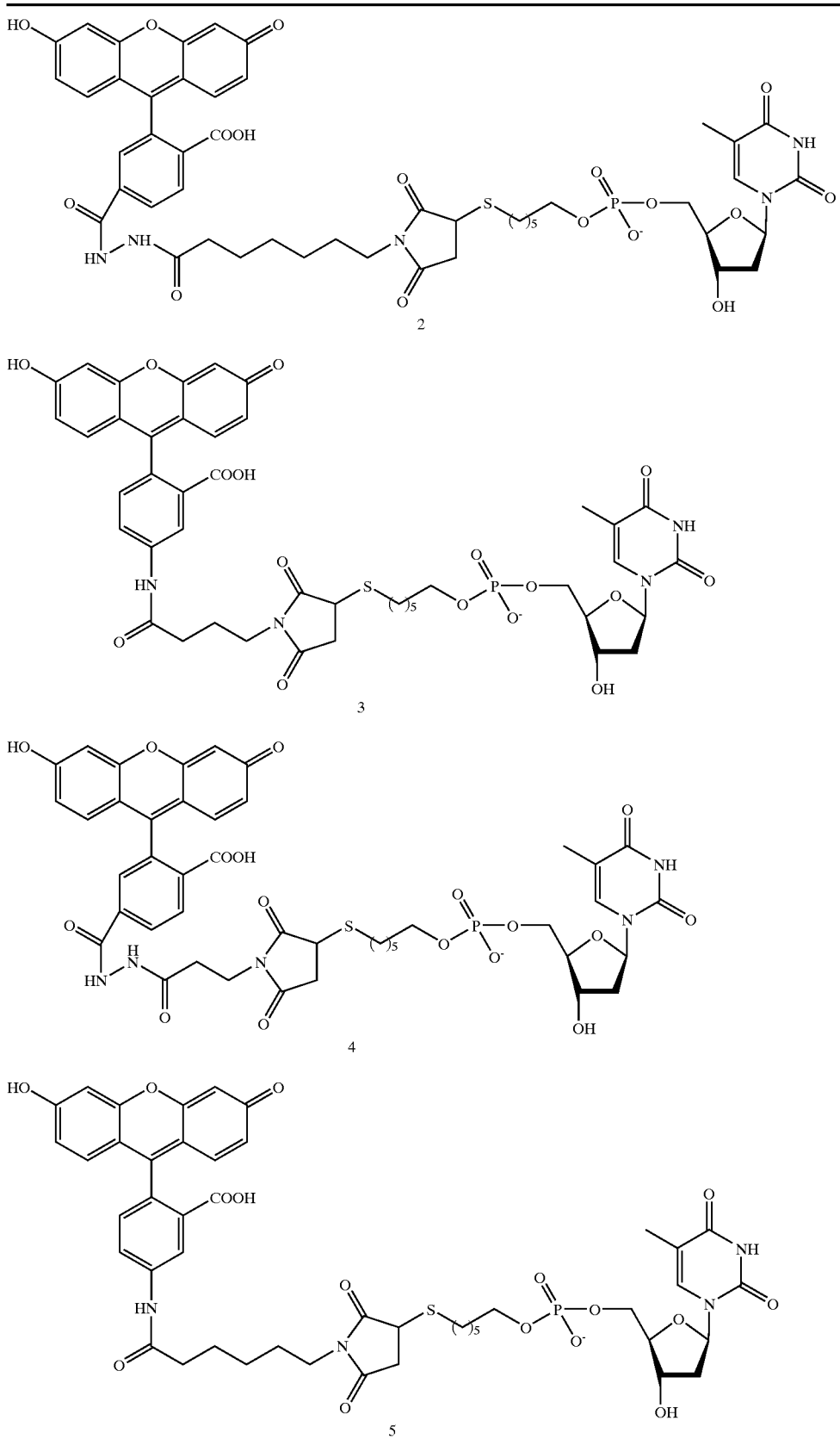

TABLE 5-continued
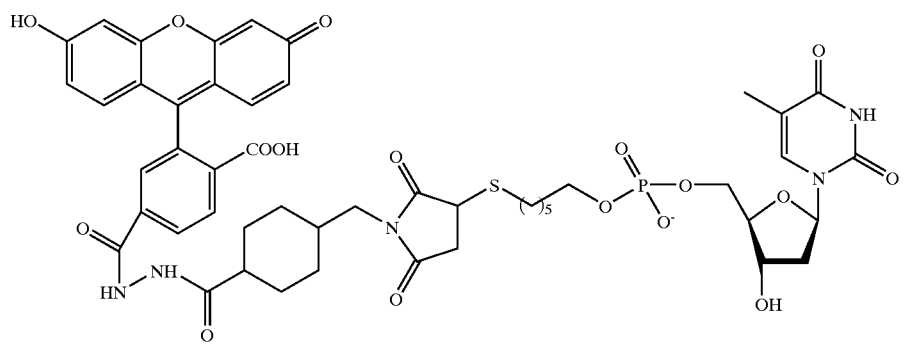
6
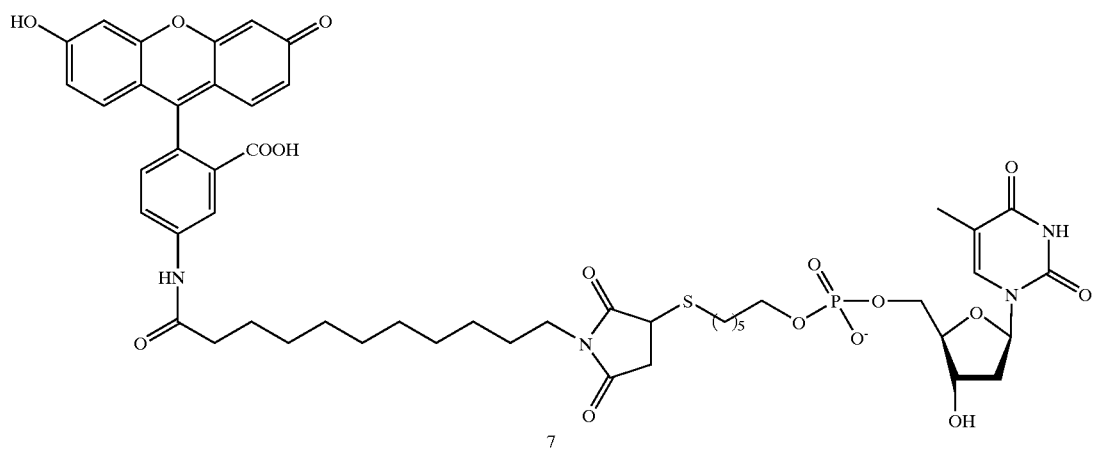
7
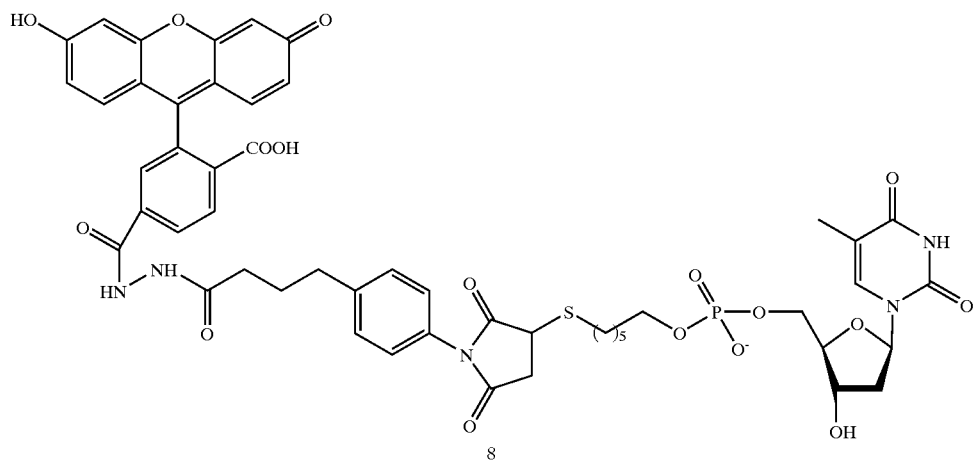
8

TABLE 5-continued

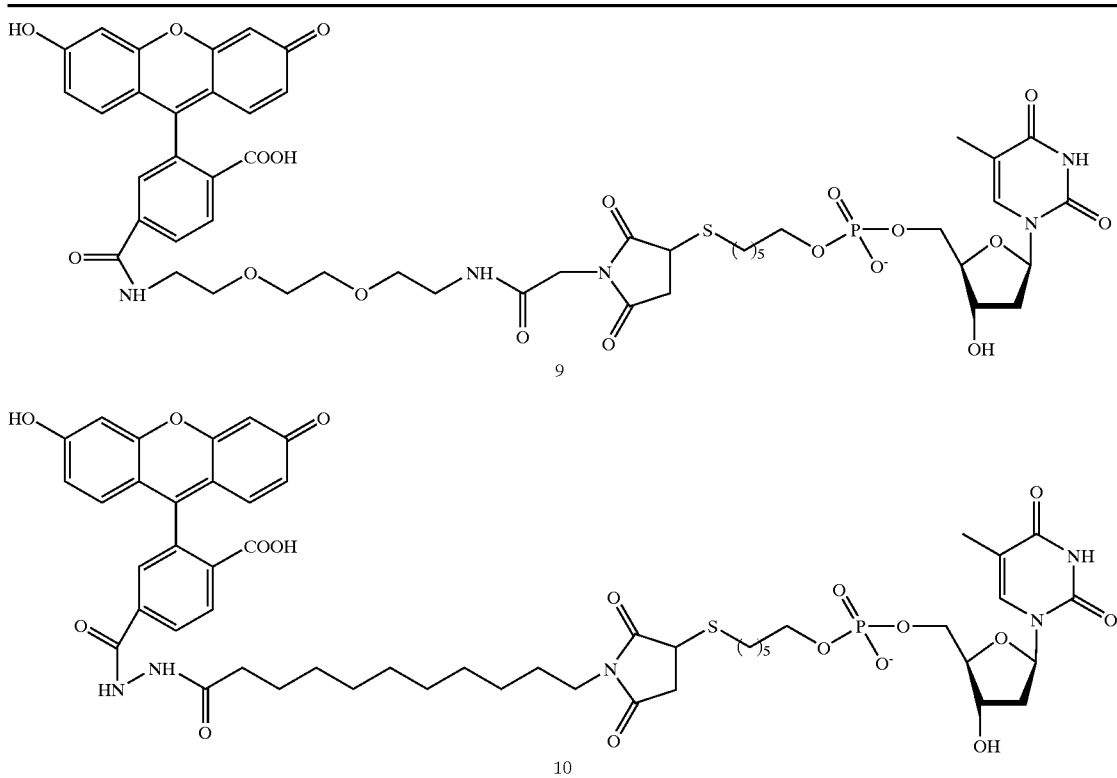

Table 5. Electrophoretic Tags derived from maleimide linked precursors.

As a matter of convenience, predetermined amounts of reagents employed in the present invention can be provided in a kit in packaged combination. A kit can comprise in packaged combination an oligonucleotide primer for each polynucleotide suspected of being in said set wherein each of said primers is hybridizable to a first sequence of a respective polynucleotide if present, a template dependent polynucleotide polymerase, nucleoside triphosphates, and a set of oligonucleotide snp detection sequences, each of said oligonucleotide probes having a fluorescent label at its 5'-end and having a sequence at its 5'-end that is hybridizable to a respective polynucleotide wherein each of said labels is cleavable from said oligonucleotide probe.

The kit may further comprise a device for conducting capillary electrophoresis. The label is cleavable by a template dependent polynucleotide polymerase having 5' to 3' exonuclease activity. The kit can further include various buffered media, some of which may contain one or more of the above reagents.

The relative amounts of the various reagents in the kits can be varied widely to provide for concentrations of the reagents necessary to achieve the objects of the present invention. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit. The kits may also include a written description of a method in accordance with the present invention as described above.

In one embodiment of the kit, the electrophoretic tags are fluorescent conjugates represented by the formula:

R—L—T wherein R is a fluorescer, L is a linking group, as described previously, and T is a functionality for binding to a nucleoside base, purine or pyrimidine, or a nucleoside base, a nucleoside, nucleotide or nucleotide triphosphate.

In another embodiment of a kit, the electrophoretic tags are fluorescent conjugates represented by the formula:

R'—L'—T' wherein R' is a fluorescer, L' is a bond an amino acid or a peptide or combinations of amino acids and thioacids or other carboxylic acids and T' is a nucleotide or nucleotide triphosphate In another embodiment of a kit, the electrophoretic tag is a fluorescent conjugate represented by the formula:

Fluorescer-L"-(amino acid)$_n$ wherein L" is a bond or a linking group of from 1 to 20 atoms in the chain and n is 1 to 100. The fluorescer may be fluorescein, the amino acid may be lysine and L" may be a bond in the form of an amide linkage involving the meta-carboxyl of the fluorescein and the terminal amine group of lysine.

In another embodiment of a kit in accordance with the invention, the electrophoretic tag is a label conjugate represented by the formula:

Fluorescein-(CO)NH—CH(CH$_2$)$_3$CH(NH$_2$)COX wherein X is selected from the group consisting of: OH, NH-lysine, NH-(lysine)$_2$, NH-alanine, NH-aspartic acid, NH-(aspartic acid)$_2$, NH-(aspartic acid)$_3$, NH-(aspartic acid)$_4$, NH-(aspartic acid)$_5$, NH-(aspartic acid)$_6$, NH-(aspartic acid)$_7$, NH-alanine-lysine, NH-aspartic acid-lysine, NH-(aspartic acid)$_2$-lysine, NH-(aspartic acid)$_3$-lysine, NH-(aspartic acid)$_4$-lysine, NH-(aspartic acid)$_5$-lysine, NH-(aspartic acid)$_6$-lysine, NH-(aspartic acid)$_7$-lysine, NH-(aspartic acid)$_8$-lysine, NH-(lysine)$_4$, and NH-(lysine)$_5$.

The kits will usually have at least about 5 different electrophoretic tags for conjugation, more usually at least about 10, frequently at least about 25 and may have 50 or more, usually not more than about 1,000. The electrophoretic tags will differ as to mobility, including mass/charge ratio and nature of charge, e.g. overall positive or negative, detectable moiety, e.g. fluorophore, electrochemical, etc, or functionality for linking a detectable moiety, e.g. maleimide, mercaptan, aldehyde, ketone, etc.

The electrophoretic tags described above may terminate in an appropriate functionality for linking to a nucleotide or nucleotide triphosphate or may terminate in such moieties.

EXAMPLES

The invention is demonstrated further by the following illustrative examples. Parts and percentages are by weight unless otherwise indicated. Temperatures are in degrees Centigrade (° C.) unless otherwise specified. The following preparations and examples illustrate the invention but are not intended to limit its scope. Unless otherwise indicated, oligonucleotides and peptides used in the following examples were prepared by synthesis using an automated synthesizer and were purified by gel electrophoresis or HPLC.

The following abbreviations have the meanings set forth below:

Tris HCl—Tris(hydroxymethyl)aminomethane-HCl (a 10x solution) from BioWhittaker, Walkersville, Md.
HPLC—high performance liquid chromatography
BSA—bovine serum albumin from Sigma Chemical Company, St. Louis Mo.
EDTA—ethylenediaminetetetraacetate from Sigma Chemical Company
bp—base pairs
g—grams
mM—millimolar
TET—tetrachlorofluorescein
FAM—fluorescein
TAMRA—tetramethyl rhodamine Reagents TET and FAMRA were purchased from Perkin Elmer (Foster City, Calif.) as were conjugates of TET, FAM and TAMRA with oligonucleotides.
Master Mix (2x): 20 mM Tris-HCl, 2.0 mM EDTA, pH 8.0 (8% Glycerol), 10 mM
MgCl$_2$, dATP 400 $\mu$M, dCTP 400 $\mu$M, dGTP 400 $\mu$M, dUTP 400 $\mu$M, AmpliTaq Gold® 0.1 U/$\mu$l (from Perkin Elmer), Amperase UNG® 0.02 U/$\mu$l (from Perkin Elmer)
Probes and Primers: (10x)
Forward Primer: 3.5 $\mu$M 5'-TCA CCA CAT CCC AGT G-3' (SEQ ID NO: 1)
Reverse Primer 2.0 $\mu$M 5'-GAG GGA GGTTTG GCTG-3' (SEQ ID NO:2)
Plasmid Allele 1 Probe: 2.0 $\mu$M (200 nM per reaction)
  5' TET-CCA GCA ACC AAT GAT GCC CGT T-TAMRA-3' (SEQ ID NO:3)
Plasmid Allele 2 Probe: 2.0 $\mu$M (200 nM per reaction)
  5' FAM-CCA GCA AGC ACT GAT GCC TGT T-TAMRA-3' (SEQ ID NO:4)
Target DNA
  Plasmid Atlele-1: 10 fg/$\mu$l=approximately 1000 copies/$\mu$l
  Plasmid Allele-2: 10 fg/$\mu$l=approximately 1000 copies/$\mu$l Example 1

The experiment Was Set Up to Run in the Following Fashion (6 Samples, a Triplicate for Allele1 and Another Triplicate for Allele-2)

22 $\mu$l of Mastermix
13 $\mu$l of probes and primers (both the probes are present)
4.0 $\mu$l of Allele-1 or Allele-2
11 $\mu$l of buffer (10 mM Tris-HCl, 1 mM EDTA, pH8.0)

The above volumes were added to a PCR tubes and the reaction mixtures were cycled in the following fashion for 40 cycles.

Initial Steps

The reaction mixtures were kept at 50° C. for 2 minutes for optimal AmpErase UNG activity. The 10 minute, 95° C. step was required to activate AmpliTaq Gold DNA Polymerase.

Each of the 40 cycles was performed on a Gene Amp® system 9600 thermal cycler (Perkin Elmer) in the following fashion:

| Melt | Anneal/Extend/Cleave |
|---|---|
| 15 seconds | 60 seconds |
| 95° C. | 60° C. |

Figure 2A:
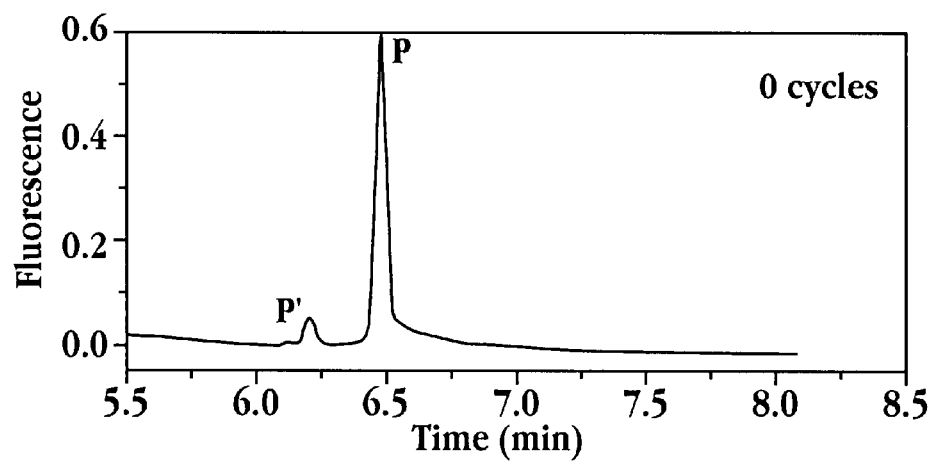
FIGS. 2A and B depict the CE separation of the reaction products of Allele 1 after 0 and 40 cycles. CE instrument: Beckman P/ACE/5000 with LIF detection. BGE: 2.5% LLD 30, 7M urea, 1×TBE. Capillary: 100 μm i.d., 375 μm o.d., Lc=27 cm, Ld=6.9 cm. Detection; $\lambda_{ex}$=488 nm, $\lambda_{em}$=520 nm. Injection: 5 s at 2.0 kV. Field strength: 100V/cm at rt. Peaks: P=unreacted snp detection sequence, P'=snp detection sequence product FIGS. 3A and B depict the CE separation of the reaction products of Allele 1 after 0 and 40 cycles. Experimental conditions are the same as FIG. 2, except for BGE composition; 2. % LDD30, 1×TBE.
Figure 2B:
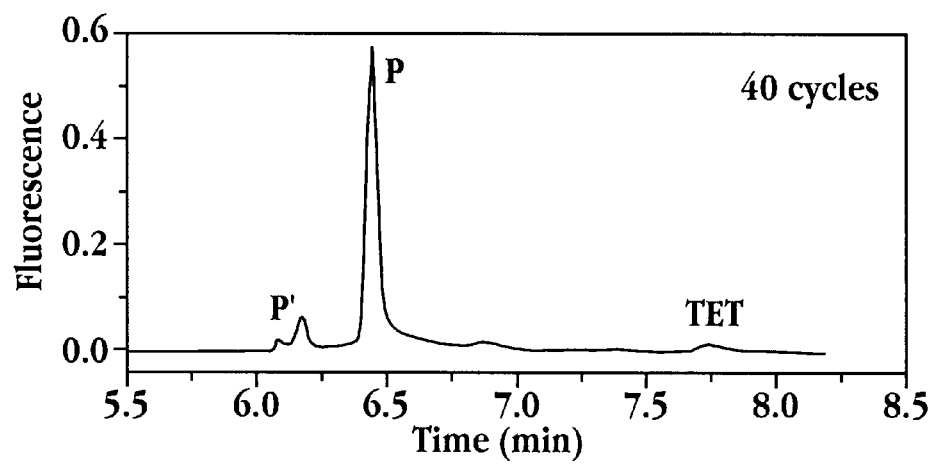

Results from experiments with Allele-1 are shown in FIG. 2. CE separation of the reaction products of Allele 1 after 0 and 40 cycles. CE instrument was Beckman P/ACE 5000 with LIF detection. BGE: 2.5% LDD30, 7 M urea, 1xTBE. Capillary: 100 $\mu$m i.d., 375 $\mu$m o.d., Lc=27 cm, Ld=6.9 cm. Detection: $\lambda$ex=488 nm, $\lambda$em=520 nm. Injection: 5 s at 2.0 kV. Field strength: 100 V/cm at room temperature. Peaks: P=unreacted primer, P'=primer product.

Figure 3A:
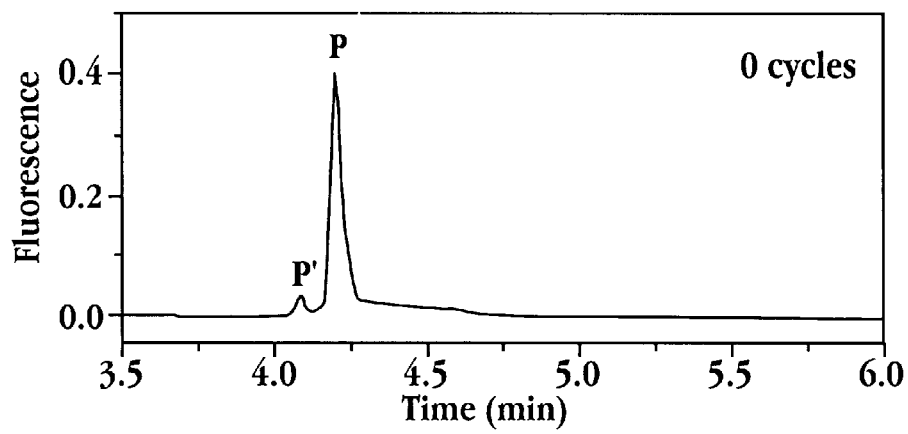
Figure 3B:
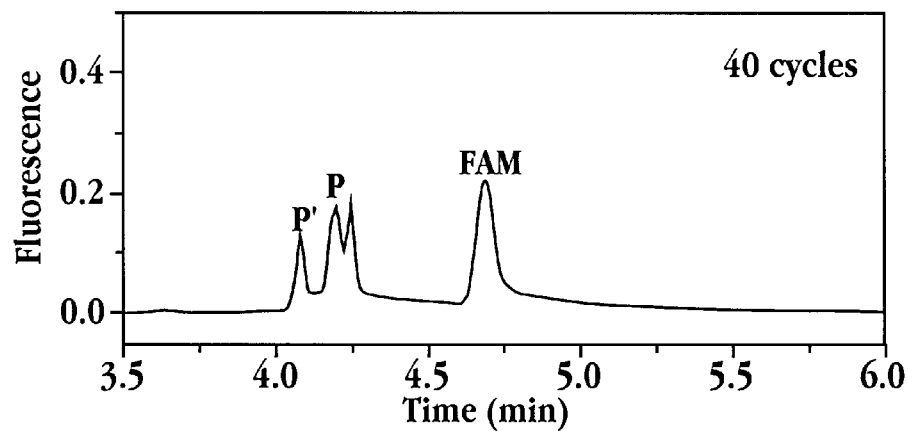

Results from experiments with Allele-2 are shown in FIG. 3. CE separation of the reaction products of Allele 2 after 0 and 40 cycles. Experimental conditions were as given above for FIG. 2 experiment except for BGE composition: 2.0% LDD30, 1xTBE.

Example 2

A multiplexed Reaction with Both Allele 1 and Allele 2 Present in Equal Ratio

The experiment was set up in the following fashion (3 reaction tubes, a triplicate).

22 $\mu$l of Mastermix
13 $\mu$l of probes and primers (both of the probes were present)

4.0 µl of Allele-1
4.0 µl of Allele-2
7 µl of buffer (10 mM Tris-HCl, 1 mM EDTA, pH8.0)
The above volumes were added to a PCR tubes and the reaction mixtures were cycled in the following fashion for 40 cycles.
Initial Steps
The reaction mixtures are kept at 50° C. for 2 minutes for optimal AmpErase UNG activity. The 10 minute, 95° C. step is required to activate AmpliTaq Gold DNA Polymerase.

Each of the 40 cycles is performed in the following fashion

| Melt | Anneal/Extend/Cleave |
|---|---|
| 15 seconds 95° C. | 60 seconds 60° C. |

Figure 4:
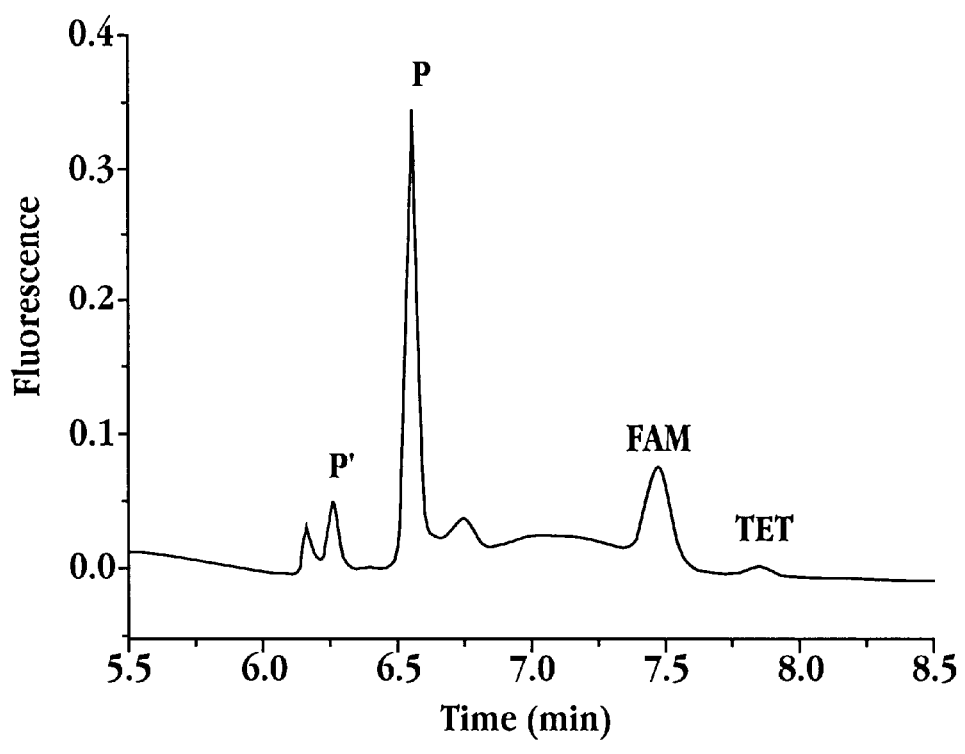
FIG. 4 is a graph of the CE separation of a 1:1 mixture of the 40 cycles products of Alleles 1 and 2, with experimental conditions as described for FIG. 2.

The results are shown in FIG. 4. CE separation of a 1:1 mixture of the 40 cycles products of Alleles 1 and 2. Experimental conditions were as given above for the experiments of FIG. 2.

Example 3

A Multiplexed Reaction with Both Allele 1 and Allele 2: Allele 1 is 10 Times More Concentrated than Allele 2

The experiment was set up in the following fashion (3 reaction tubes, a triplicate)

22 µl of Mastermix
13 µl of probes and primers (both the probes were present)
5.0 µl of Allele 1
0.5 µl of Allele 2
9.5 µl of buffer (10 mM Tris-HCl, 11 mM EDTA, pH8.0)
The above volumes were added to respective PCR tubes and the reaction mixtures were cycled in the following fashion for 40 cycles.
Initial Steps
The reaction mixtures were kept at 50° C. for 2 minutes for optimal AmpErase UNG activity. The 10 minute 95° C. step was required to activate AmpliTaq Gold DNA Polymerase.
Each of the 40 cycles is performed in the following fashion

| Melt | Anneal/Extend/Cleave |
|---|---|
| 15 seconds 95° C. | 60 seconds 60° C. |

Figure 5:
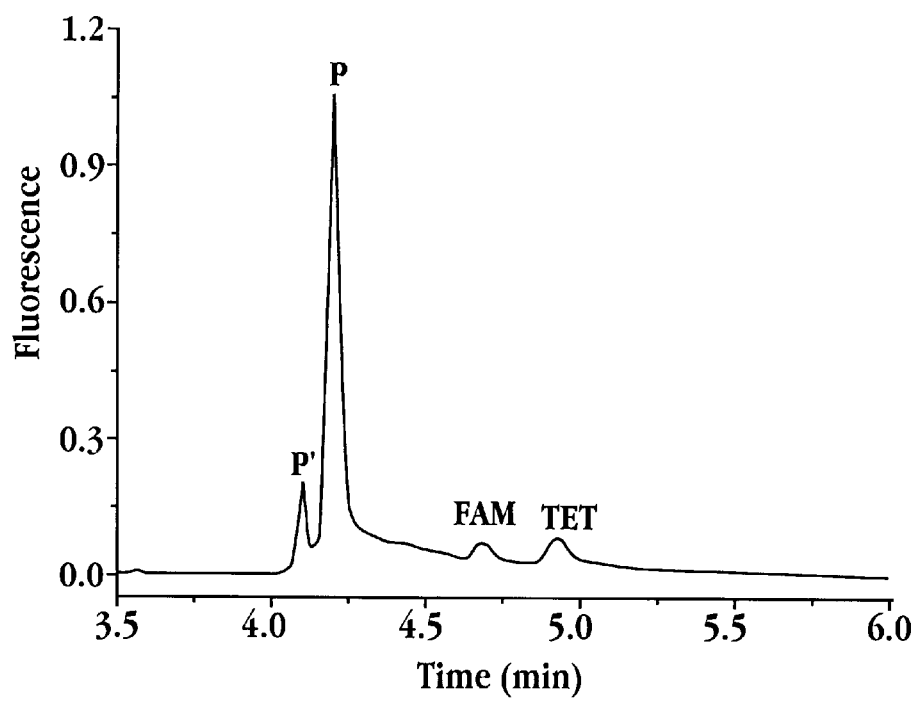
FIG. 5 is a graph of the CE separation of a 1:10 mixture of the 40 cycles products of Alleles 1 and 2, with experimental conditions as described for FIG. 2.

The results are shown in FIG. 5. CE separation of a 1:10 mixture of the 40 cycles products of Alleles 1 and 2. Experimental conditions were as given for the experiments of FIG. 2.

Example 5

Electroseparation of Label Conjugates on Microfluidic Chip

Label conjugates comprising fluorescein linked to three different peptides, namely, KKAA (SEQ ID NO: 5), KKKA (SEQ ID NO: 6) and KKKK (SEQ ID NO: 7) were prepared as follows: The protected tetrapeptide was prepared on resin using Merrifield reagents. The N-terminus of the last amino acid was reacted with fluorescein N-hydroxysuccinimide (Molecular Probes). The peptides were cleaved from the resin and purified by high performance liquid chromatography (HPLC).

Figure 6:
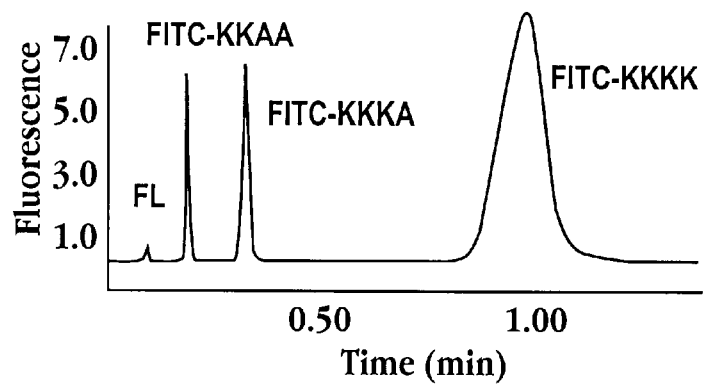
FIG. 6 is an electopherogram of electrophoretic tags which involved a separation involving a 1000-fold difference in concentration.
Figure 7A:
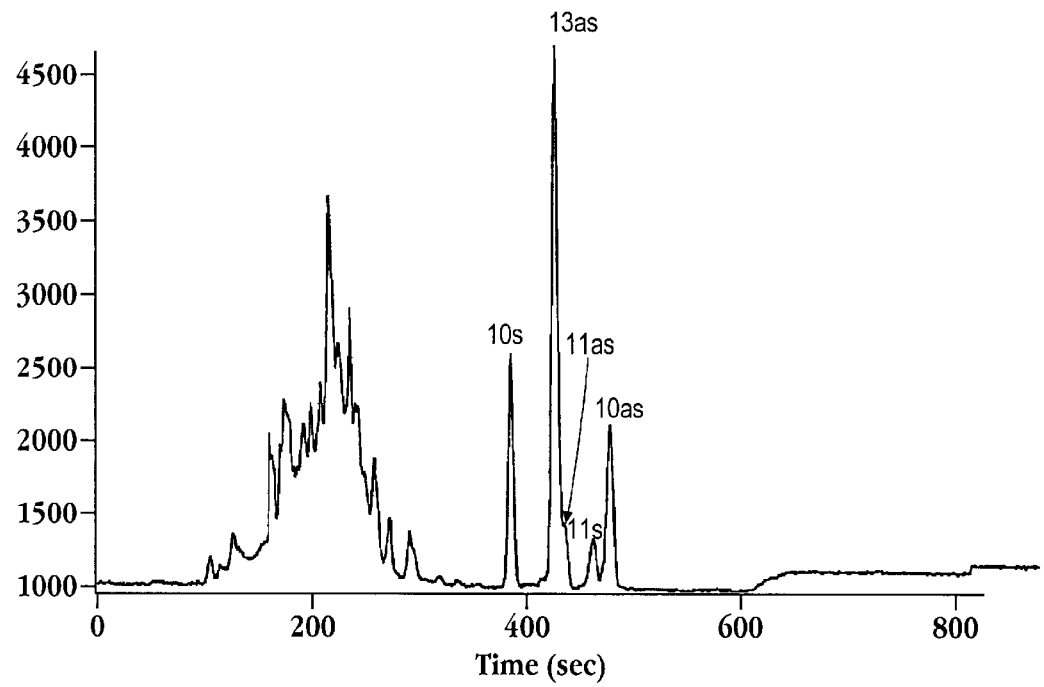
FIG. 7A is an electropherogram of the analysis of 5 snps of the cystic fibrosis genes using multiplexed PCR and the subject E-TAG probes.
Figure 7B:
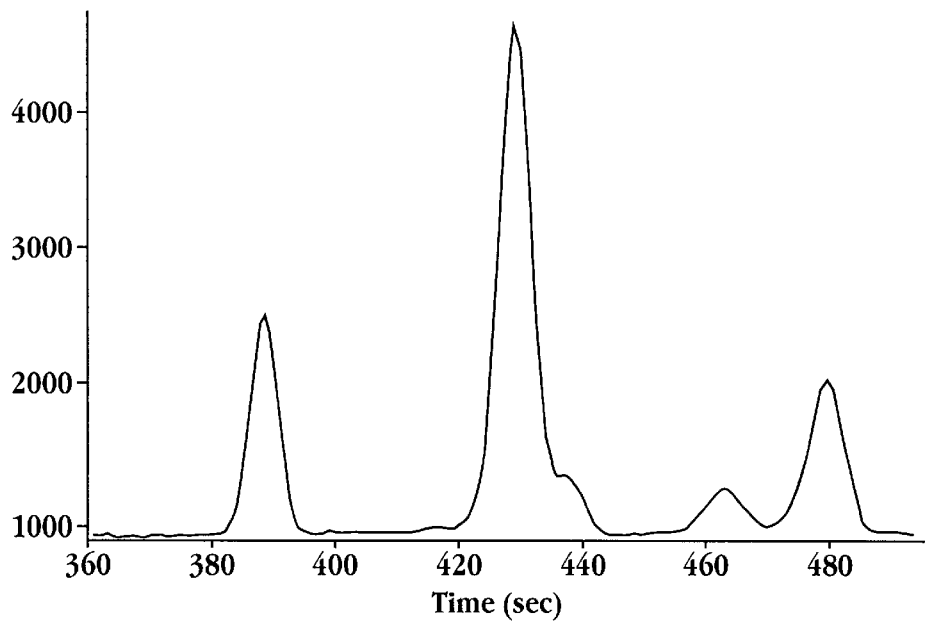
FIG. 7B shows an expanded electrophoretic tag region from 380–500 seconds of the electropherogram of FIG. 7A.
Figure 7C:
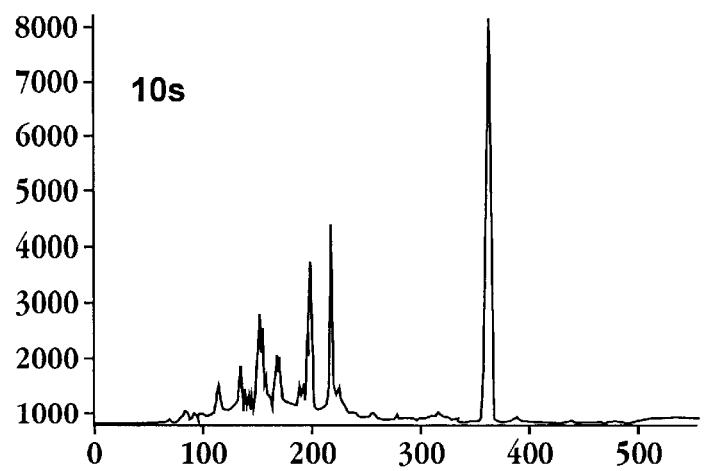
FIGS. 7C–7E are each electropherograms of a single-plex PCR of the cystic fibrosis gene using E-TAG probes.
Figure 7D:
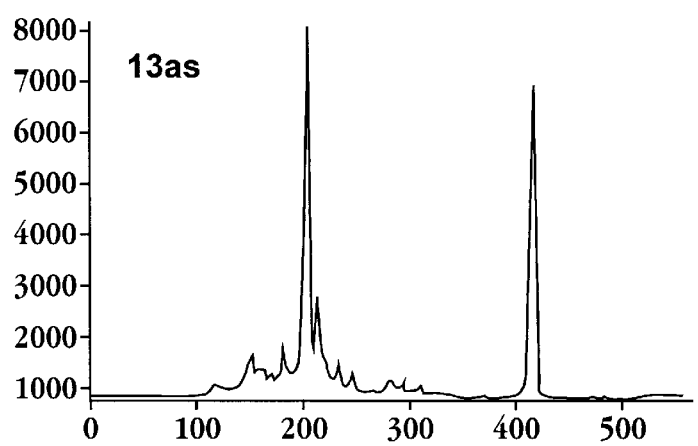
Figure 7E:
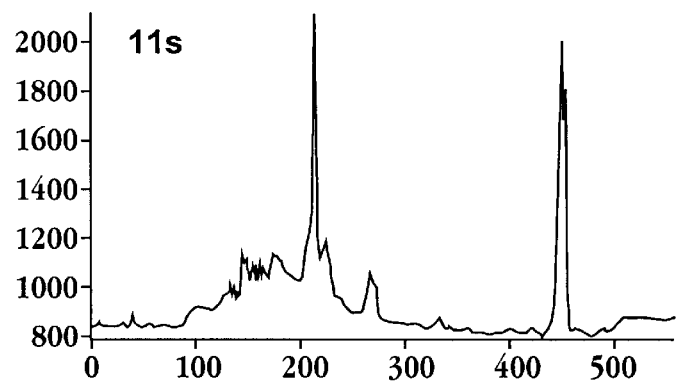
Figure 7F:
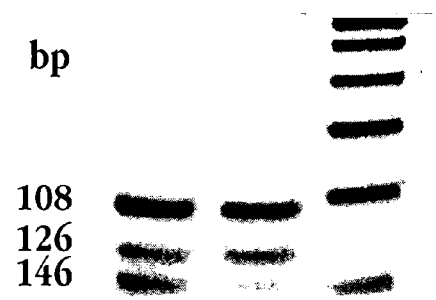
FIG. 7F is an agarose gel separation of fragments from the triplex PCR.
Figure 7G:
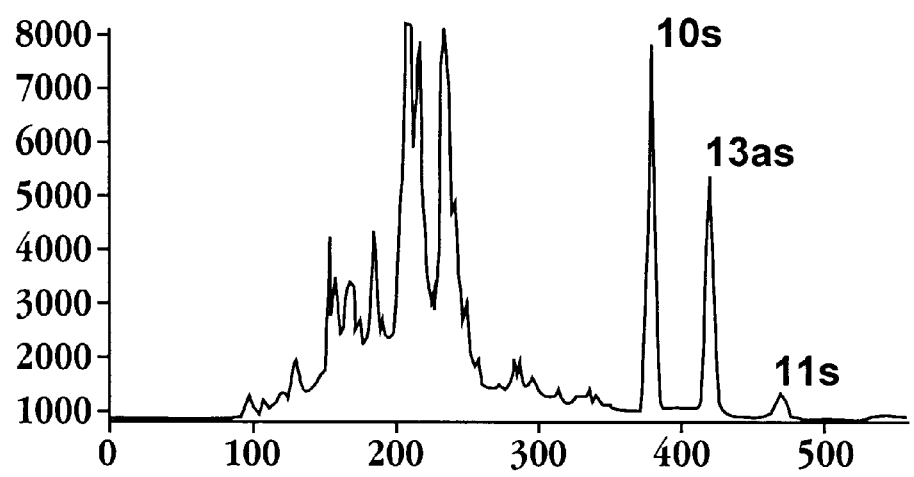
FIG. 7G is an electropherogram of the triplex PCR of the cyctic fibrosis gene using E-TAG probes.

The label conjugates prepared as described above and fluorescein were combined in an aqueous buffered and were separated and detected in an electrophoresis chip. Detection was 0.5 cm for the injection point on the anodal side of an electrophoresis channel. FITC-KKKK exhibited negative charge and FITC-KKKA and FITC-KKKK exhibited positive charge as determined by the migration time relative to EOF. The net charge of FITC-KKKK was greater than +1 and FITC-KKKA and FITC-KKKK migrated electrophoretically against the EOF. The results are shown in FIG. 6.

Example 6

Capillary Electrophoresis of CFTR PCR Products with E-TAG Probes on ABI 310

The following example demonstrates separation in a gel based capillary electrophoresis of cleavage of a probe. The conditions employed were: Gel: 2.5% LDD30 in 1×TBE with 7M urea; CE: PE ABI 310; Capillary: 47 cm long; 36 cm to window; 75 um ID; Running Buffer: 1×TBE. (LDD30 is a linear copolymer of N,N-diethyl acrylamide and N,N-dimethylacrylamide, 70:30).

The ABI310 was set up in accordance with the directions of the manufacturer.

The parameters used were: Inj Secs 5; Inj kV 2.0; Run kV 9.4; Run C 45; Run Time 10 min. To determine the relationship of where each probe separated, a spike in system was used. First one digested probe was separated and its peak site determined, then a second probe was spiked into the first probe and the two separated. Then, a third probe was spiked in and separated, and so on till the sites of all the six probes was determined. The single plex PCR runs were first separated followed by separation of the multiplex PCR, which was compared to the S1 digested separation.

| Sample* | Type of probe | Probe conc. (nM) | vol (ul) |
|---|---|---|---|
| 10s FAM-T | 32mer | 20 | 10 |
| 10s FAM-T | dig | 20 | 10 |
| 10s FAM-T | pcr | 80 | 5 |
| 10as HEX-T | 32mer | 20 | 10 |
| 10as HEX-T | dig | 20 | 10 |
| 10as HEX-T | pcr | 80 | 5 |
| 11s HEX-A | 28mer | 20 | 10 |
| 11s HEX-A | dig | 20 | 10 |
| 11s HEX-A | pcr | 80 | 5 |
| 11as TET-C | 28mer | 20 | 10 |
| 11as TET-C | dig | 20 | 10 |
| 11as TET-C | pcr | 80 | 5 |
| 13s FAM-C | 23mer | 20 | 10 |
| 13s FAM-C | dig | 20 | 10 |
| 13s FAM-C | pcr | 80 | 5 |
| 13as TET-A | 23mer | 20 | 10 |
| 13as TET-A | dig | 20 | 10 |

-continued

| Sample* | Type of probe | Probe conc. (nM) | vol (ul) |
|---|---|---|---|
| 13as TET-A | pcr | 80 | 5 |
| MP10s11s13as | pcr | 80 | 5 |
| MP10as11as13a | pcr | 80 | 5 |
| MP10s10as11s11as13s13as | pcr | 80 | 5 | dig—S1 nuclease digestion; pcr—amplification; * the particular samples are found in the above table, where as exemplary 10s FAM-T intends Exon 10 sense, which is referred to as CF7, so that one looks to CF7 for the probe sequence, FAM intends fluorescein, and T is the nucleotide to which the fluorescein is attached. For the other symbols, "as" is the antisense sequence, HEX is hexachlorofluorescein, TET is tetrachlorofluorescein, and when more than one exon is indicated, the reaction mixture is multiplexed under the conditions described below.

Example 7

Taq DNA Polymerase exhibits 5' to 3' exonuclease activity in which hybridized probes on the template DNA are cleaved during PCR. In the subject example, sequence specific probes with fluorescent dye attached to the 5' were employed. PCR was performed with these probes in a reaction and then separation performed in a gel based capillary electrophoresis to determine the cleavage of the probe.

Primers, Probes, Mutation

| Name | Location_SNP | Mutation | SNP |
|---|---|---|---|
| CF1 | Exon 11 | R553X | C1789T |
| CF2 | Exon 19 | R1162X | C3616T |
| CF4 | Exon 3 | G85E | G386A |
| CF5 | Exon 4 | R117H | G482A |
| CF6 | Exon 7 | R347P | G1172C |
| CF7 | Exon 10 | V520F | G1690T |
| CF8 | Exon 11 | 542X | G1756T |
| CF9 | Exon 11 | G551D | G1784A |
| CF10* | Exon 11 | R560T | G1811C |
| CF11* | Exon 18 | D1152H | G3586C |
| CF13* | Exon 22 | G1349D | G4178A |

| Name | Hyb_probe_length | Probe_seq | Probe_antisense |
|---|---|---|---|
| CF1HYB | 26 | GTGGAGGTCAACGAGCAAGAATTTCT (SEQ ID NO: 8) | AGAAATTCTTGCTCGTTGACCTCCAC (SEQ ID NO: 30) |
| CF2HYB | 25 | AGATGCGATCTGTGAGCCGAGTCTT (SEQ ID NO: 9) | AAGACTCGGCTCACAGATCGCATCT (SEQ ID NO: 31) |
| CF4HYB | 32 | TTCTGGAGATTTATGTTCTATGGAATCTTTTT (SEQ ID NO: 10) | AAAAAGATTCCATAGAACATAAATCTCCAGAA (SEQ ID NO: 32) |
| CF5HYB | 21 | AAGGAGGAACGCTCTATCGCG (SEQ ID NO: 11) | CGCGATAGAGCGTTCCTCCTT (SEQ ID NO: 33) |
| CF6HYB | 20 | ATTGTTCTGCGCATGGCGGT (SEQ ID NO: 12) | ACCGCCATGCGCAGAACAAT (SEQ ID NO: 34) |
| CF7HYB | 25 | ATACAGAAGCGTCATCAAAGCATGC (SEQ ID NO: 13) | GCATGCTTTGATGACGCTTCTGTAT (SEQ ID NO: 35) |
| CF8HYB | 29 | CAATATAGTTCTTGGAGAAGGTGGAATCA (SEQ ID NO: 14) | TGATTCCACCTTCTCCAAGAACTATATTG (SEQ ID NO: 36) |
| CF9HYB | 26 | CTGAGTGGAGGTCAACGAGCAAGAAT (SEQ ID NO: 15) | ATTCTTGCTCGTTGACCTCCACTCAG (SEQ ID NO: 37) |
| CF10HYB* | 32 | TTCCATTTTCTTTTTAGAGCAGTATACAAAGA (SEQ ID NO: 16) | TCTTTGTATACTGCTCTAAAAAGAAAATGGAA (SEQ ID NO: 38) |
| CF11HYB* | 28 | AAACTCCAGCATAGATGTGGATAGCTTG (SEQ ID NO: 17) | CAAGCTATCCACATCTATGCTGGAGTTT (SEQ ID NO: 39) |
| CF13HYB* | 23 | CTAAGCCATGGCCACAAGCAGTT (SEQ ID NO: 18) | AACTGCTTGTGGCCATGGCTTAG (SEQ ID NO: 40) |

| Name | product_size | forward_seq | Reverse_seq |
|---|---|---|---|
| CF1PF/R | 198 | CCTTTCAAATTCAGATTGAGCATAC (SEQ ID NO: 19) | TTTACAGCAAATGCTTGCTAGAC (SEQ ID NO: 41) |
| CF2PF/R | 127 | TGTGAAATTGTCTGCCATTCTTA (SEQ ID NO: 20) | GGTTTGGTTGACTTGGTAGGTTA (SEQ ID NO: 42) |
| CF4PF/R | 239 | TCTTTTGCAGAGAATGGGATAGA (SEQ ID NO: 21) | TGGAGTTGGATTCATCCTTTATATT (SEQ ID NO: 43) |
| CF5PF/R | 151 | CCAAAGCAGTACAGCCTCTCTTA (SEQ ID NO: 22) | CCAAAAATGGCTGGGTGTAG (SEQ ID NO: 44) |
| CF6PF/R | 137 | TCTGTGCTTCCCTATGCACTAA (SEQ ID NO: 23) | CCAAGAGAGTCATACCATGTTTGTA (SEQ ID NO: 45) |
| CF7PF/R | 146 | TGGAGCCTTCAGAGGGTAAA (SEQ ID NO: 24) | TGCTTTGATGACGCTTCTGTA (SEQ ID NO: 46) |

-continued

| | | | |
|---|---|---|---|
| CF8PF/R | 198 | CCTTTCAAATTCAGATTGAGCAT AC (SEQ ID NO: 25) | TTTACAGCAAATGCTTGCTAG C (SEQ ID NO: 47) |
| CF9PF/R | 198 | CCTTTCAAATTCAGATTGAGCAT AC (SEQ ID NO: 26) | TTTACAGCAAATGCTTGCTAG AC (SEQ ID NO: 48) |
| CF10PF/R* | 108 | GACCAGGAAATAGAGAGGAAATG TA (SEQ ID NO: 27) | CATCTAGGTATCCAAAAGGAG AGTCTA (SEQ ID NO: 49) |
| CF11PF/R* | 188 | GAAGGAGAAGGAAGAGTTGGTAT TAT C (SEQ ID NO: 28) | CGGTATATAGTTCTTCCTCATG CTATT (SEQ ID NO: 50) |
| CF13PF/R* | 138 | TTGGGCTCAGATCTGTGATAG (SEQ ID NO: 29) | GCAAGATCTTCGCCTTACTG (SEQ ID NO: 51) |

| Name | Name | m_prob, Tm_forward, m_reverse, oC | forward_length, reverse_length |
|---|---|---|---|
| CF1HYB | CF1PF/R | 66.83, 60.36, 58.7 | 25, 23 |
| CF2HYB | CF2PF/R | 68.65, 59.64, 60.5 | 23, 24 |
| CF4HYB | CF4PF/R | 64.24, 60.21, 59. | 23, 25 |
| CF5HYB | CF5PF/R | 65.06, 60.08, 60.3 | 23, 20 |
| CF6HYB | CF6PF/R | 68.18, 59.9, 59.4 | 22, 25 |

The procedure employed in carrying out the Single-plex PCR reaction was as follows:

1. Make up Master Mix

| 1x | 6.5x | |
|---|---|---|
| 13.2 ul | 85.8 ul | Water |
| 3 ul | 19.5 ul | 25 mM MgCl2 |
| 2.5 ul | 16.25 ul | 10x PCR Buffer |
| 1 ul | 6.5 ul | 20 ng/ul DNA template |
| 0.2 ul | 1.3 ul | 25 mM dNTPs |
| 0.3 ul | 1.95 ul | 5 u/ul Taq Gold (this is added just prior to start of reaction) |

2. Aliquot 0.8 ul of 5 uM probe and 4 ul of 10 uM primer set to PCR tubes.

| 3. Primer sets | Probe |
|---|---|
| 10s | CF10s |
| 10as | CF10as |
| 11s | CF11s |
| 11as | CF11as |
| 13s | CF13s |
| 13as | CF13as |

4. Aliquot 20.2 ul of the Master Mix to each tube.
5. In a PE2400 cycler,
   96 C.; 10 MIN
   35 CYCLES
     95 C.; 10 SEC
     55 C.; 30 SEC
     70 C.; 45 SEC
   35 CYCLES
   70 C.; 10 MIN
   4 C.; 24 hours
6. After PCR, run the 2.5 ul of each sample on a 2.5% agarose gel.
7. EtBr stain the gel, take image with camera equipped UV source.

Results clearly demonstrated the formation of a unique electrophretic tag with distinct mobility (Table 1) for each amplified sequence.

Multiplex Amplification of CFTR Fragments with E-TAG Probes

In this study the reaction involved a plurality of probes in the same PCR reaction mixture for different snps in CFTR. In the subject system, sequence specific probes with fluorescent dye attached to the 5' terminus of the probe were employed. PCR was performed with these probes and then separation performed in gel based capillary electrophoresis to determine the cleavage of the probe. The following table indicates the fragment, the mutation reference and the specific nucleotide difference and number inb the sequence.

The procedure employed for performing the multiplex amplification was as follows:

Make up Master Mix

| 1x | 2.2x | |
|---|---|---|
| 8 ul | 17.6 ul | 25 mM MgCl2 |
| 2.5 ul | 5.5 ul | 10x PCR Buffer |
| 8 ul | 17.6 ul | 10 ng/ul DNA template |
| .2 ul | .44 ul | 25 mM dNTPs |
| 1 ul | 2.2 ul | 5 ul/ul Taq Gold (this is added just prior to start of reaction) |

8. Aliquot 0.8 ul of each 5 uM probes CF10s, CF11s, CF10as, CF11as, CF13as and 1 ul of each 10 uM primer sets 10s, 11s, 10as, 11as, 13as in one PCR tube.
9. Aliquot 19.7 ul of the Master Mix to each tube.
10. In a PE2400 cycler,
    96 C.; 10 MIN
    40 CYCLES
      95 C.; 10 SEC
      55 C.; 30 SEC
      65 C.; 1 MIN
    40 CYCLES
    70 C.; 10 MIN
    4 C.; storage
11. After PCR, The amplified products were separated as described in the previous section. The results are shown in FIG. 7. Even in the multiplexed amplification each detection probe gives rise to a unique electrophoretic tag with distinct mobility.

Example 8

Electroseparation of Nine Electrophoretic Tags on Microfluidic Chip

Label conjugates comprising 9 different fluorescein derivatives linked to thymine, (Table 5; 1–9): Poly deoxy thymidine (20-mer; with a 5' thiol group) is reacted with different maleamide functionalized fluoresceins. After the reaction the product is ethanol precipitated. In a reaction of 12 l in volume, 10 l of 25 M oligo, 1.0 l 10× S1 nuclease reaction buffer, 1 l of S1 nuclease, incubate at 37 °C. for 30 min followed by 96 °C. for 25 min. The digested fragments are purified by HPLC.

Figure 8:
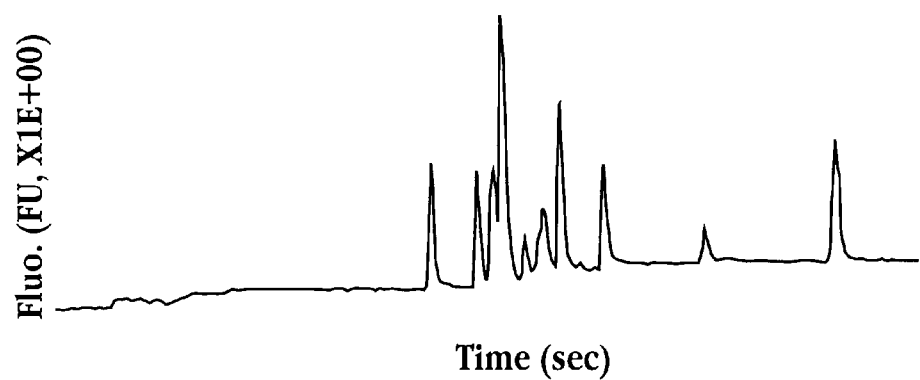
FIG. 8 is an electropherogram of a separation of 9 negatively charged E-TAG probes.

The nine different electrophoretic tags prepared as described above and fluorescein were combined in an aqueous buffered and were separated and detected in an electrophoresis chip. Detection was 0.5 cm for the injection point on the anodal side of an electrophoresis channel. The results are shown in FIG. 8.

Example 9

RT-PCR Conditions

Ten ul from a total volume of 25 uls of each mRNA was analyzed in a total volume of 50 uls containing 0.5 uM of each of the oligonucleotide primers, 0.2 mM of each dNTP, 100 nM of each E-TAG labeled oligonucleotide probe, 1×RT PCR buffer, 2.5 mM MgCl2, 0.1 U/ul Tfl DNA polymerase and 0.1 U/ul AMV Reverse Transcriptase (Promega Access, RT-PCR system).

Reverse Transcription was performed for 45 minutes at 48° C. followed by PCR. (40 thermal cycles of 30 s at 94' C., 1 min at 60' C. and 2 min at 69° C. mRNA was obtained from M. Williams, Genentech Inc. Probe and primer design was performed as described in Analytical Biochemistry, 270, 41–49 (1999). Phosphorothioates were attached to 2, 3,4 and 5 phosphate moieties from the 5' end. Separation was performed as described in the previous section.

Figure 9A:
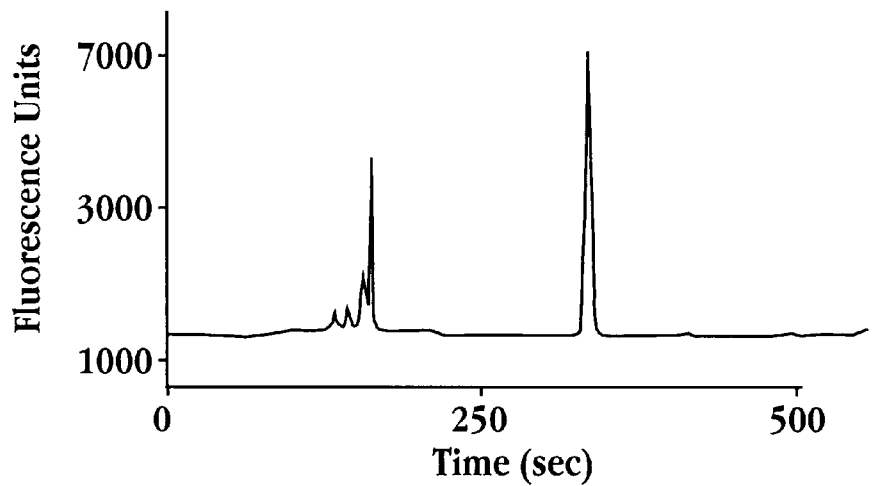
FIGS. 9A–9D are electropherograms of probes employing a penultimate thiophosphate linkage in the E-TAG probes to discourage cleavage after the first phosphate linkage.

FIG. 9a: Demonstrates the formation of 5 different cleavage products in the PCR amplification of ANF with electrophoretic tag labeled at the 5' end of the sequence detection probe. In the second experiment, phosphate group at 2,3,4 and 5 position is converted into thiophosphate group. PCR amplification of ANF using thiophospate modified sequence detection probe yield only one cleavage product.

Figure 9B:
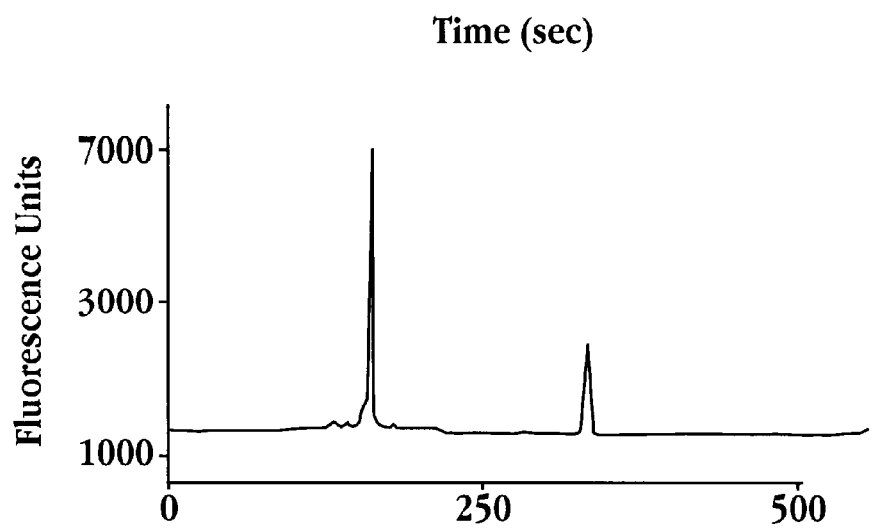
Figure 9C:
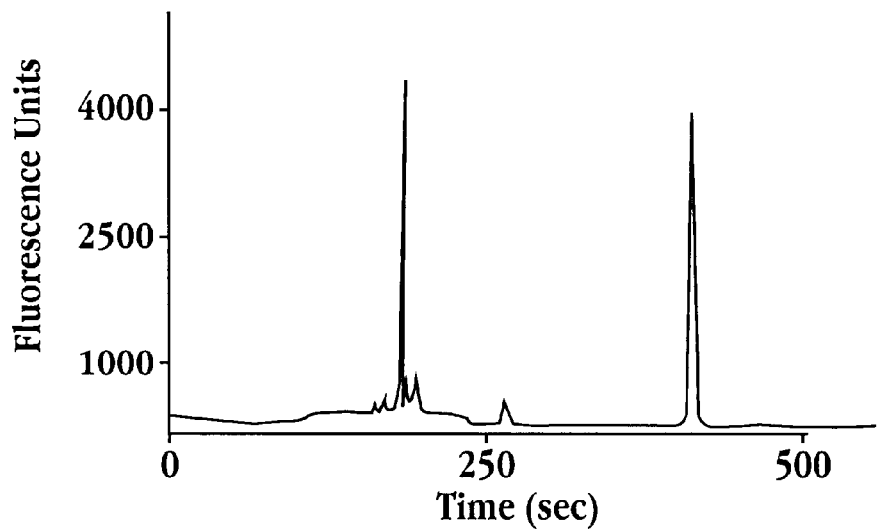
Figure 9D:
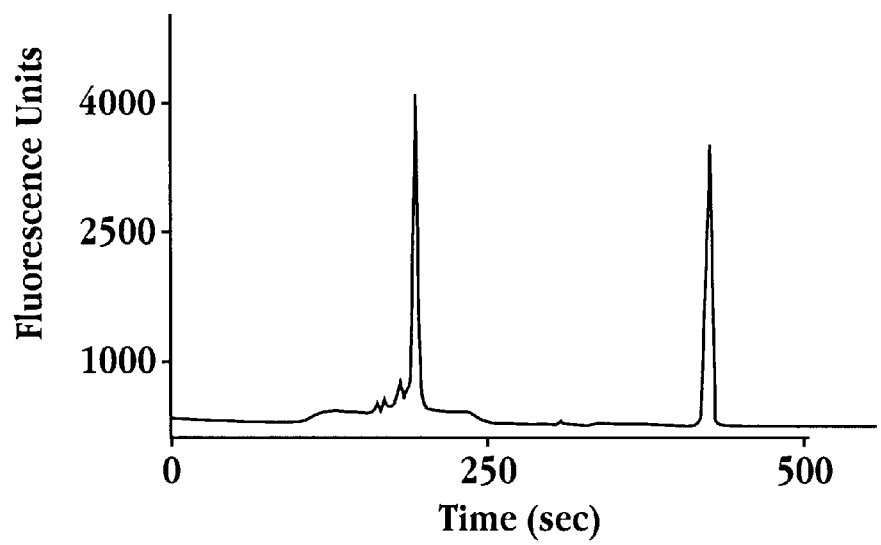

FIG. 9b Demonstrates the formation of 3 different cleavage products in the PCR amplification of GAPDH with electrophoretic tag labeled at the 5' end of the sequence detection probe. In the second experiment, phosphate group at 2 and 3 position is converted into thiophosphate group. PCR amplification of ANF using thiophospate modified sequence detection probe yield only one predominant cleavage product.

Results clearly demonstrate that for two different genes that thiophosphates prevent cleavage at multiple sites of detection probes. A single detectable entity (a single electrophoretic tag: FIGS. 9a and 9b) is generated as a consequence of amplification reaction.

General Procedure for Synthesis of 6-Carboxyfluorescein Phosphoramidite Derivatives To a solution of 6-carboxyfluorescein (0.5 g, 1.32 mmol) in dry pyridine (5 mL) was added dropwise, isobutyric anhydride (0.55 mL, 3.3mmol). The reaction was allowed to stir at room temperature under an atmosphere of nitrogen for 3 h. After removal of pyridine in vacuo the residue was redissolved in ethyl acetate (150 mL) and washed with water (150 mL). The organic layer was separated, dried over $Na_2SO_4$, filtered, and concentrated in vacuo to yield a brownish residue. This material was dissolved in $CH_2Cl_2$ (5 mL) after which N-hydroxy succinimide (0.23 g, 2.0 mmol) and dicyclohexylcarbodiimide (0.41 g, 1.32 mmol) were added. The reaction was allowed to stir at room temperature for 3 h and then filtered through a fritted funnel to remove the white solid, which had formed. To the filtrate was added aminoethanol (0.12 mL, 2.0 mmol) dissolved in 1 mL of $CH_2Cl_2$. After 3 h the reaction was again filtered to remove a solid which had formed and then diluted with additional $CH_2Cl_2$ (50 mL). The solution was washed with water (150 mL) and then separated. The organic layer was dried over $Na_2SO_4$, filtered, and concentrated in vacuo to yield a white foam (0.7 g, 95%, 3 steps). $^1$H NMR: (DMSO) 8.68 (t, 1H), 8.21 (d, 1H), 8.14 (d, 1H), 7.83 (s, 1H), 7.31 (s, 2H), 6.95 (s, 4H), 4.69 (t, 1H), 3.45 (q, 2H), 3.25 (q, 2H), 2.84 (h, 2H), 1.25 (d, 12H). Mass (LR FAB$^+$) calculated for $C_{31}H_{29}NO_9$ (M+H$^+$) 559.2, found: 560.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting at least one nucleic acid sequence in a target nucleic acid sample, said method comprising:

combining under primer extension conditions: a polymerase having 5'-3' exonuclease activity, said target DNA and a reagent pair consisting of a primer and a detection sequence comprised of nucleotide bases for each DNA sequence to be determined, wherein each said primer specifically binds to said target DNA and said detection sequence binds to said target DNA downstream from said primer in the direction of primer extension, wherein each said detection sequence is characterized by having an electrophoretic tag specific for each said DNA sequence and at least one nucleotide linkage at positions immediately 3' of the second nucleotide at the 5'-end of said oligonucleotide that is resistant to nuclease hydrolysis;

executing at least one cycle of said primer extension, whereby said detection sequence bound to target DNA is at least partially degraded with release of said electrophoretic tag substantially free of said detection sequence, such that cleavage of the detection sequence at its 5' end by the 5'-3' exonuclease produces a single released product composed of the electrophoretic tag and the 5'-end nucleotide of the detection sequence, wherein each said released product produced from a given detection sequence has a known, unique electrophoretic mobility with respect to the released products produced from all other such detection sequences, by virtue of a unique charge/mass ratio associated with the electrophoretic tag;

separating said released products into individual fractions of released products specific for each DNA sequence; and detecting, by means of said released product, said fractions, whereby the presence in said target DNA sample of said at least one DNA sequence is detected.

2. A method according to claim 1, wherein a plurality of said pairs are combined for determining a plurality of single nucleotide polymorphisms ("snps") in said target DNA, wherein said detection sequences bind at the site of said snps.

3. A method according to claim 1, wherein said executing comprises a plurality of cycles.

4. A method according to claim 1, comprising the additional step of reacting said electrophoretic tag with a fluorophore after release of said released product.

5. A method according to claim 1, wherein said electrophoretic tag comprises a neutral linker of from 1 to 60 carbon atoms.

6. A method according to claim 1, wherein said electrophoretic tag comprises a charged linker of from 1 to 60 carbon atoms.

7. A method according to claim 1, wherein said detection sequence comprises a linkage resistant to exonuclease hydrolysis between at least the second and third bases and optionally successive bases in the direction of degradation.

8. A method for detecting a plurality of single nucleotide polymorphisms ("snps") in a target DNA sample, said method comprising:

combining under primer extension conditions: a polymerase having 5'-3' exonuclease activity; said target DNA and a reagent pair consisting of primer and snp detection sequence for each snp, wherein said primer specifically binds to said target DNA and said snp detection sequence binds to said target DNA at the site of said snp downstream from said primer in the direction of primer extension, wherein said snp detection sequence is characterized by having an electrophoretic tag with a detectable label;

executing a plurality of cycles of said primer extension, whereby said snp detection sequences bound to target DNA are partially degraded with release of said electrophoretic tag, such that cleavage of the detection sequence at its 5' end by the 5'-3' exonuclease produces a single released product composed of the electrophoretic tag and the 5'-end nucleotide of the detection sequence, wherein each said released product produced from a given detection sequence has a known, unique electrophoretic mobility with respect to the released products produced from all other such detection sequences, by virtue of a unique charge/mass ratio associated with the electrophoretic tag;

separating said released product into separate bands by means of capillary electrophoresis; and detecting said bands of released product, whereby snps in said sample DNA are detected.

9. A method according to claim 8, wherein said pair have a combined total of at least 36 nucleotides.

10. A method according to claim 8, wherein said snp detection sequence is further characterized by comprising a quencher, which quenches said fluorophore when bound to said snp detection sequence, and including the further step of monitoring the change in fluorescence during said executing.

11. A method according to claim 8, wherein said snp detection sequences are within 200 nucleotides of said primer when bound to said target DNA.

12. A method according to claim 8, wherein said snp detection sequence comprises a positively charged moiety.

13. A method according to claim 12, wherein said charged moiety comprises at least one of lysine, arginine and histidine.

14. In a method according to claim 1, where the electrophoretic tags all have the same number of nucleotides bound to said electrophoretic tag, the improvement which comprises:

providing a mixture of electrophoretic tags having the same number of nucleotides bound to the electrophoretic tag by:

the electrophoretic tags having the penultimate linkage and optionally successive linkages of said detection sequence nuclease resistant to hydrolysis;

said electrophoretic tag is labeled at the penultimate or terminal nucleotide with a label that binds to a positively charged receptor, and including the additional step of combining said released electrophoretic tags with said positively charged receptor and separating said electrophoretic tags into fractions by electrophoresis; or said electrophoretic tag is labeled at the penultimate nucleotide or terminal nucleotide with a label that binds to a receptor, and including the additional step of combining said released electrophoretic tags with said receptor, and including the additional step of separating electrophoretic tags having the same number of nucleotides by means of said receptor.

15. A method according to claim 1, further including a ligand attached to the penultimate nucleotide of the detection sequence.

16. A method according to claim 15 where the ligand is biotin.

* * * * *

SEQUENCE LISTING

<160> NUMBER OF SEQ ID NOS: 53

<210> SEQ ID NO 1
<211> LENGTH: 16
<212> TYPE: DNA
<213> ORGANISM: Artificial Sequence
<220> FEATURE:
<223> OTHER INFORMATION: primer

<400> SEQUENCE: 1
tcaccacatc ccagtg                    16

<210> SEQ ID NO 2

```
<211> LENGTH: 16
<212> TYPE: DNA
<213> ORGANISM: Artificial Sequence
<220> FEATURE:
<223> OTHER INFORMATION: primer

<400> SEQUENCE: 2
gagggaggtt tggctg                                                      16

<210> SEQ ID NO 3
<211> LENGTH: 22
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)...(1)
<223> OTHER INFORMATION: 5' nucleotide linked to tetrachlorofluorescein
<220> FEATURE:
<221> NAME/KEY: misc_feature
<222> LOCATION: (22)...(22)
<223> OTHER INFORMATION: 3' nucleotide linked to tetramethyl rhodamine

<400> SEQUENCE: 3
ccagcaacca atgatgcccg tt                                               22

<210> SEQ ID NO 4
<211> LENGTH: 22
<212> TYPE: DNA
<213> ORGANISM: Artificial Sequence
<220> FEATURE:
<223> OTHER INFORMATION: probe
<220> FEATURE:
<221> NAME/KEY: misc_binding
<222> LOCATION: (1)...(1)
<223> OTHER INFORMATION: 5' nucleotide linked to fluorescein
<220> FEATURE:
<221> NAME/KEY: misc_binding
<222> LOCATION: (22)...(22)
<223> OTHER INFORMATION: 3' nucleotide linked to tetramethyl rhodamine

<400> SEQUENCE: 4
ccagcaagca ctgatgcctg tt                                               22

<210> SEQ ID NO 5
<211> LENGTH: 4
<212> TYPE: PRT
<213> ORGANISM: Artificial Sequence
<220> FEATURE:
<223> OTHER INFORMATION: peptide linker

<400> SEQUENCE: 5

Lys Lys Ala Ala
 1

<210> SEQ ID NO 6
<211> LENGTH: 4
<212> TYPE: PRT
<213> ORGANISM: Artificial Sequence
<220> FEATURE:
<223> OTHER INFORMATION: peptide linker

<400> SEQUENCE: 6

Lys Lys Lys Ala
 1

<210> SEQ ID NO 7
<211> LENGTH: 4
```

```
<212> TYPE: PRT
<213> ORGANISM: Artificial Sequence
<220> FEATURE:
<223> OTHER INFORMATION: peptide linker

<400> SEQUENCE: 7

Lys Lys Lys Lys
 1

<210> SEQ ID NO 8
<211> LENGTH: 26
<212> TYPE: DNA
<213> ORGANISM: Artificial Sequence
<220> FEATURE:
<223> OTHER INFORMATION: probe

<400> SEQUENCE: 8
gtggaggtca acgagcaaga atttct                                          26

<210> SEQ ID NO 9
<211> LENGTH: 25
<212> TYPE: DNA
<213> ORGANISM: Artificial Sequence
<220> FEATURE:
<223> OTHER INFORMATION: probe

<400> SEQUENCE: 9
agatgcgatc tgtgagccga gtctt                                           25

<210> SEQ ID NO 10
<211> LENGTH: 32
<212> TYPE: DNA
<213> ORGANISM: Artificial Sequence
<220> FEATURE:
<223> OTHER INFORMATION: probe

<400> SEQUENCE: 10
ttctggagat ttatgttcta tggaatcttt tt                                   32

<210> SEQ ID NO 11
<211> LENGTH: 21
<212> TYPE: DNA
<213> ORGANISM: Artificial Sequence
<220> FEATURE:
<223> OTHER INFORMATION: probe

<400> SEQUENCE: 11
aaggaggaac gctctatcgc g                                               21

<210> SEQ ID NO 12
<211> LENGTH: 20
<212> TYPE: DNA
<213> ORGANISM: Artificial Sequence
<220> FEATURE:
<223> OTHER INFORMATION: probe

<400> SEQUENCE: 12
attgttctgc gcatggcggt                                                 20

<210> SEQ ID NO 13
<211> LENGTH: 25
<212> TYPE: DNA
<213> ORGANISM: Artificial Sequence
<220> FEATURE:
<223> OTHER INFORMATION: probe

<400> SEQUENCE: 13
```

```
atacagaagc gtcatcaaag catgc                                      25

<210> SEQ ID NO 14
<211> LENGTH: 29
<212> TYPE: DNA
<213> ORGANISM: Artificial Sequence
<220> FEATURE:
<223> OTHER INFORMATION: probe

<400> SEQUENCE: 14
caatatagtt cttggagaag gtggaatca                                  29

<210> SEQ ID NO 15
<211> LENGTH: 26
<212> TYPE: DNA
<213> ORGANISM: Artificial Sequence
<220> FEATURE:
<223> OTHER INFORMATION: probe

<400> SEQUENCE: 15
ctgagtggag gtcaacgagc aagaat                                     26

<210> SEQ ID NO 16
<211> LENGTH: 32
<212> TYPE: DNA
<213> ORGANISM: Artificial Sequence
<220> FEATURE:
<223> OTHER INFORMATION: probe

<400> SEQUENCE: 16
ttccattttc ttttagagc agtatacaaa ga                               32

<210> SEQ ID NO 17
<211> LENGTH: 28
<212> TYPE: DNA
<213> ORGANISM: Artificial Sequence
<220> FEATURE:
<223> OTHER INFORMATION: probe

<400> SEQUENCE: 17
aaactccagc atagatgtgg atagcttg                                   28

<210> SEQ ID NO 18
<211> LENGTH: 23
<212> TYPE: DNA
<213> ORGANISM: Artificial Sequence
<220> FEATURE:
<223> OTHER INFORMATION: probe

<400> SEQUENCE: 18
ctaagccatg gccacaagca gtt                                        23

<210> SEQ ID NO 19
<211> LENGTH: 25
<212> TYPE: DNA
<213> ORGANISM: Artificial Sequence
<220> FEATURE:
<223> OTHER INFORMATION: probe

<400> SEQUENCE: 19
cctttcaaat tcagattgag catac                                      25

<210> SEQ ID NO 20
<211> LENGTH: 23
<212> TYPE: DNA
```

<213> ORGANISM: Artificial Sequence
<220> FEATURE:
<223> OTHER INFORMATION: probe

<400> SEQUENCE: 20
tgtgaaattg tctgccattc tta                                              23

<210> SEQ ID NO 21
<211> LENGTH: 23
<212> TYPE: DNA
<213> ORGANISM: Artificial Sequence
<220> FEATURE:
<223> OTHER INFORMATION: probe

<400> SEQUENCE: 21
tcttttgcag agaatgggat aga                                              23

<210> SEQ ID NO 22
<211> LENGTH: 23
<212> TYPE: DNA
<213> ORGANISM: Artificial Sequence
<220> FEATURE:
<223> OTHER INFORMATION: probe

<400> SEQUENCE: 22
ccaaagcagt acagcctctc tta                                              23

<210> SEQ ID NO 23
<211> LENGTH: 22
<212> TYPE: DNA
<213> ORGANISM: Artificial Sequence
<220> FEATURE:
<223> OTHER INFORMATION: probe

<400> SEQUENCE: 23
tctgtgcttc cctatgcact aa                                               22

<210> SEQ ID NO 24
<211> LENGTH: 20
<212> TYPE: DNA
<213> ORGANISM: Artificial Sequence
<220> FEATURE:
<223> OTHER INFORMATION: probe

<400> SEQUENCE: 24
tggagccttc agagggtaaa                                                  20

<210> SEQ ID NO 25
<211> LENGTH: 25
<212> TYPE: DNA
<213> ORGANISM: Artificial Sequence
<220> FEATURE:
<223> OTHER INFORMATION: probe

<400> SEQUENCE: 25
cctttcaaat tcagattgag catac                                            25

<210> SEQ ID NO 26
<211> LENGTH: 25
<212> TYPE: DNA
<213> ORGANISM: Artificial Sequence
<220> FEATURE:
<223> OTHER INFORMATION: probe

<400> SEQUENCE: 26
cctttcaaat tcagattgag catac                                            25

<210> SEQ ID NO 27
<211> LENGTH: 25
<212> TYPE: DNA
<213> ORGANISM: Artificial Sequence
<220> FEATURE:
<223> OTHER INFORMATION: probe

<400> SEQUENCE: 27
gaccaggaaa tagagaggaa atgta                                              25

<210> SEQ ID NO 28
<211> LENGTH: 27
<212> TYPE: DNA
<213> ORGANISM: Artificial Sequence
<220> FEATURE:
<223> OTHER INFORMATION: probe

<400> SEQUENCE: 28
gaaggagaag gaagagttgg tattatc                                            27

<210> SEQ ID NO 29
<211> LENGTH: 21
<212> TYPE: DNA
<213> ORGANISM: Artificial Sequence
<220> FEATURE:
<223> OTHER INFORMATION: probe

<400> SEQUENCE: 29
ttgggctcag atctgtgata g                                                  21

<210> SEQ ID NO 30
<211> LENGTH: 26
<212> TYPE: DNA
<213> ORGANISM: Artificial Sequence
<220> FEATURE:
<223> OTHER INFORMATION: probe antisense

<400> SEQUENCE: 30
agaaattctt gctcgttgac ctccac                                             26

<210> SEQ ID NO 31
<211> LENGTH: 25
<212> TYPE: DNA
<213> ORGANISM: Artificial Sequence
<220> FEATURE:
<223> OTHER INFORMATION: probe antisense

<400> SEQUENCE: 31
aagactcggc tcacagatcg catct                                              25

<210> SEQ ID NO 32
<211> LENGTH: 32
<212> TYPE: DNA
<213> ORGANISM: Artificial Sequence
<220> FEATURE:
<223> OTHER INFORMATION: probe antisense

<400> SEQUENCE: 32
aaaaagattc catagaacat aaatctccag aa                                      32

<210> SEQ ID NO 33
<211> LENGTH: 21
<212> TYPE: DNA
<213> ORGANISM: Artificial Sequence
<220> FEATURE:

-continued

<223> OTHER INFORMATION: probe antisense

<400> SEQUENCE: 33
cgcgatagag cgttcctcct t                                            21

<210> SEQ ID NO 34
<211> LENGTH: 20
<212> TYPE: DNA
<213> ORGANISM: Artificial Sequence
<220> FEATURE:
<223> OTHER INFORMATION: probe antisense

<400> SEQUENCE: 34
accgccatgc gcagaacaat                                              20

<210> SEQ ID NO 35
<211> LENGTH: 25
<212> TYPE: DNA
<213> ORGANISM: Artificial Sequence
<220> FEATURE:
<223> OTHER INFORMATION: probe antisense

<400> SEQUENCE: 35
gcatgctttg atgacgcttc tgtat                                        25

<210> SEQ ID NO 36
<211> LENGTH: 29
<212> TYPE: DNA
<213> ORGANISM: Artificial Sequence
<220> FEATURE:
<223> OTHER INFORMATION: probe antisense

<400> SEQUENCE: 36
tgattccacc ttctccaaga actatattg                                    29

<210> SEQ ID NO 37
<211> LENGTH: 26
<212> TYPE: DNA
<213> ORGANISM: Artificial Sequence
<220> FEATURE:
<223> OTHER INFORMATION: probe antisense

<400> SEQUENCE: 37
attcttgctc gttgacctcc actcag                                       26

<210> SEQ ID NO 38
<211> LENGTH: 32
<212> TYPE: DNA
<213> ORGANISM: Artificial Sequence
<220> FEATURE:
<223> OTHER INFORMATION: probe antisense

<400> SEQUENCE: 38
tctttgtata ctgctctaaa aagaaaatgg aa                                32

<210> SEQ ID NO 39
<211> LENGTH: 28
<212> TYPE: DNA
<213> ORGANISM: Artificial Sequence
<220> FEATURE:
<223> OTHER INFORMATION: probe antisense

<400> SEQUENCE: 39
caagctatcc acatctatgc tggagttt                                     28

```
<210> SEQ ID NO 40
<211> LENGTH: 23
<212> TYPE: DNA
<213> ORGANISM: Artificial Sequence
<220> FEATURE:
<223> OTHER INFORMATION: probe antisense

<400> SEQUENCE: 40
aactgcttgt ggccatggct tag                                            23

<210> SEQ ID NO 41
<211> LENGTH: 23
<212> TYPE: DNA
<213> ORGANISM: Artificial Sequence
<220> FEATURE:
<223> OTHER INFORMATION: probe

<400> SEQUENCE: 41
tttacagcaa atgcttgcta gac                                            23

<210> SEQ ID NO 42
<211> LENGTH: 24
<212> TYPE: DNA
<213> ORGANISM: Artificial Sequence
<220> FEATURE:
<223> OTHER INFORMATION: probe

<400> SEQUENCE: 42
ggtttggttg acttggtagg ttta                                           24

<210> SEQ ID NO 43
<211> LENGTH: 25
<212> TYPE: DNA
<213> ORGANISM: Artificial Sequence
<220> FEATURE:
<223> OTHER INFORMATION: probe

<400> SEQUENCE: 43
tggagttgga ttcatccttt atatt                                          25

<210> SEQ ID NO 44
<211> LENGTH: 20
<212> TYPE: DNA
<213> ORGANISM: Artificial Sequence
<220> FEATURE:
<223> OTHER INFORMATION: probe

<400> SEQUENCE: 44
ccaaaaatgg ctgggtgtag                                                20

<210> SEQ ID NO 45
<211> LENGTH: 25
<212> TYPE: DNA
<213> ORGANISM: Artificial Sequence
<220> FEATURE:
<223> OTHER INFORMATION: probe

<400> SEQUENCE: 45
ccaagagagt cataccatgt ttgta                                          25

<210> SEQ ID NO 46
<211> LENGTH: 21
<212> TYPE: DNA
<213> ORGANISM: Artificial Sequence
<220> FEATURE:
<223> OTHER INFORMATION: probe
```

```
<400> SEQUENCE: 46
tgctttgatg acgcttctgt a                                              21

<210> SEQ ID NO 47
<211> LENGTH: 23
<212> TYPE: DNA
<213> ORGANISM: Artificial Sequence
<220> FEATURE:
<223> OTHER INFORMATION: probe

<400> SEQUENCE: 47
tttacagcaa atgcttgcta gac                                            23

<210> SEQ ID NO 48
<211> LENGTH: 23
<212> TYPE: DNA
<213> ORGANISM: Artificial Sequence
<220> FEATURE:
<223> OTHER INFORMATION: probe

<400> SEQUENCE: 48
tttacagcaa atgcttgcta gac                                            23

<210> SEQ ID NO 49
<211> LENGTH: 27
<212> TYPE: DNA
<213> ORGANISM: Artificial Sequence
<220> FEATURE:
<223> OTHER INFORMATION: probe

<400> SEQUENCE: 49
catctaggta tccaaaagga gagtcta                                        27

<210> SEQ ID NO 50
<211> LENGTH: 27
<212> TYPE: DNA
<213> ORGANISM: Artificial Sequence
<220> FEATURE:
<223> OTHER INFORMATION: probe

<400> SEQUENCE: 50
cggtatatag ttcttcctca tgctatt                                        27

<210> SEQ ID NO 51
<211> LENGTH: 20
<212> TYPE: DNA
<213> ORGANISM: Artificial Sequence
<220> FEATURE:
<223> OTHER INFORMATION: probe

<400> SEQUENCE: 51
gcaagatctt cgccttactg                                                20

<210> SEQ ID NO 52
<211> LENGTH: 21
<212> TYPE: DNA
<213> ORGANISM: Artificial Sequence
<220> FEATURE:
<223> OTHER INFORMATION: snp detection sequence
<220> FEATURE:
<221> NAME/KEY: misc_feature
<222> LOCATION: (21)...(21)
<223> OTHER INFORMATION: 3' nucleotide linked to tetramethyl rhodamine

<400> SEQUENCE: 52
cagcaaccat tgatgcccgt t                                              21
```

-continued

```
<210> SEQ ID NO 53
<211> LENGTH: 21
<212> TYPE: DNA
<213> ORGANISM: Artificial Sequence
<220> FEATURE:
<223> OTHER INFORMATION: snp detection sequence
<220> FEATURE:
<221> NAME/KEY: misc_feature
<222> LOCATION: (21)...(21)
<223> OTHER INFORMATION: 3' nucleotide linked to tetramethyl rhodamine

<400> SEQUENCE: 53
cagcaagcac tgatgcctgt t                                              21
```